(12) United States Patent
Daniels

(10) Patent No.: US 9,468,590 B2
(45) Date of Patent: Oct. 18, 2016

(54) EMULSIFIER-FREE, POLYMER-STABILIZED FOAM FORMULATIONS

(75) Inventor: Rolf Daniels, Rottenburg a.N. (DE)

(73) Assignee: NEUBOURG SKIN CARE GMBH & CO. KG, Greven (DE)

( * ) Notice: Subject to any disclaimer, the term of this patent is extended or adjusted under 35 U.S.C. 154(b) by 122 days.

(21) Appl. No.: 13/514,687

(22) PCT Filed: Dec. 10, 2010

(86) PCT No.: PCT/EP2010/007542
§ 371 (c)(1),
(2), (4) Date: Jun. 8, 2012

(87) PCT Pub. No.: WO2011/069674
PCT Pub. Date: Jun. 16, 2011

(65) Prior Publication Data
US 2012/0244093 A1  Sep. 27, 2012

Related U.S. Application Data

(60) Provisional application No. 61/285,252, filed on Dec. 10, 2009.

(30) Foreign Application Priority Data

Dec. 10, 2009 (EP) .................... 09015330

(51) Int. Cl.
| A61K 47/32 | (2006.01) |
|---|---|
| A61K 8/81 | (2006.01) |
| A61Q 17/04 | (2006.01) |
| C08F 226/10 | (2006.01) |
| C08F 228/02 | (2006.01) |
| A61K 8/04 | (2006.01) |
| A61K 8/06 | (2006.01) |
| A61Q 19/00 | (2006.01) |
| A61K 8/34 | (2006.01) |
| A61K 8/36 | (2006.01) |
| A61K 8/37 | (2006.01) |

(52) U.S. Cl.
CPC ............. *A61K 8/046* (2013.01); *A61K 8/062* (2013.01); *A61K 8/342* (2013.01); *A61K 8/361* (2013.01); *A61K 8/37* (2013.01); *A61K 8/8147* (2013.01); *A61K 8/8158* (2013.01); *A61K 8/8182* (2013.01); *A61Q 19/00* (2013.01); *A61K 2800/33* (2013.01)

(58) Field of Classification Search
CPC ........ A61K 8/046; A61K 8/06; A61K 8/062; A61K 8/8147; A61K 8/8158; A61K 8/8182; A61Q 19/00
USPC .................. 424/59; 514/772.6, 772.4, 772.5; 526/288, 264
See application file for complete search history.

(56) References Cited

U.S. PATENT DOCUMENTS

| 2,968,628 A | 1/1961 | Reed |
|---|---|---|
| 3,330,730 A | 7/1967 | Hernandez |
| 3,793,464 A | 2/1974 | Rusch |
| 3,970,584 A | 7/1976 | Hart et al. |
| 4,411,926 A | 10/1983 | Trumbetas et al. |
| 4,481,185 A | 11/1984 | Grollier et al. |
| 4,515,810 A | 5/1985 | Chow et al. |
| 4,551,480 A | 11/1985 | Stiefel et al. |
| 4,622,074 A | 11/1986 | Miyoshi et al. |
| 4,661,340 A | 4/1987 | Nagy née Kricsfalussy et al. |
| 4,808,388 A | 2/1989 | Beutler et al. |
| 5,525,588 A | 6/1996 | Michetti et al. |
| 5,540,853 A | 7/1996 | Trinh et al. |
| 5,616,746 A | 4/1997 | Mahieu et al. |
| 5,621,012 A | 4/1997 | Schönrock et al. |
| 5,653,970 A | 8/1997 | Vermeer |
| 5,882,660 A | 3/1999 | Chambers et al. |
| 6,033,647 A * | 3/2000 | Touzan et al. .................. 424/45 |
| 6,156,297 A | 12/2000 | Maurin et al. |
| 6,210,656 B1 | 4/2001 | Touzan et al. |
| 6,251,954 B1 | 6/2001 | Roulier et al. |
| 6,423,323 B2 | 7/2002 | Neubourg |
| 6,437,068 B2 | 8/2002 | Löffler et al. |
| 6,517,816 B1 | 2/2003 | Gonzalez et al. |
| 6,528,058 B1 | 3/2003 | Edgar et al. |
| 6,589,509 B2 | 7/2003 | Keller et al. |
| 6,605,290 B2 | 8/2003 | Roulier et al. |
| 6,645,476 B1 | 11/2003 | Morschhäuser et al. |

(Continued)

FOREIGN PATENT DOCUMENTS

| AU | 199928052 A | 11/1999 |
|---|---|---|
| AU | 764038 B2 | 8/2003 |

(Continued)

OTHER PUBLICATIONS

US 5,534,264, 07/1996, Fowler et al. (withdrawn)
Experimental Report (Versuchsbericht).
Anonymus: "Duden/sinnfallig/Rechtschreibung, Bedeutung, Definition, Synonyme", XP055086030.
Gaspar et al. "Solution structure of a modified comb-like polymer from octadecyl methacrylate and acrylic acid" Chemical Physics Letters, 348 (2001) 395-402.
Loeffler et al. "A new ph stable polymer for gels and o/w emulsions" SOFW-Journal, vol. 128, Jan. 1, 2002, pp. 46-52.

(Continued)

*Primary Examiner* — Anna Falkowitz
(74) *Attorney, Agent, or Firm* — Leydig, Voit & Mayer, Ltd.

(57) ABSTRACT

The invention relates to a foam formulation comprising a substantially emulsifier-free emulsion of the oil-in-water type, comprising an oil phase and an aqueous phase, the emulsion comprising at least one surface active, ionic polymer with a molecular weight of more than 5000 g/mol, wherein the ionic polymer is a copolymer comprising as monomer units an ionic monomer (M1) and at least one further monomer.

25 Claims, 1 Drawing Sheet

(56) References Cited

U.S. PATENT DOCUMENTS

| | | |
|---|---|---|
| 6,683,144 B2 | 1/2004 | Löffler et al. |
| 6,891,009 B2 | 5/2005 | Löffler et al. |
| 7,001,604 B2 | 2/2006 | Albrecht et al. |
| 7,015,294 B2 | 3/2006 | Dausch et al. |
| 7,060,257 B2 | 6/2006 | Göppel et al. |
| 7,208,556 B2 | 4/2007 | Löffler et al. |
| 7,482,383 B2 | 1/2009 | Scheffler |
| 8,536,380 B2 | 9/2013 | Scheffler |
| 8,586,639 B2 | 11/2013 | Gottschalk-Gaudig |
| 8,828,444 B2 | 9/2014 | Scheffler |
| 2001/0029287 A1 | 10/2001 | Loffler et al. |
| 2001/0033826 A1 | 10/2001 | Roulier et al. |
| 2001/0049419 A1 | 12/2001 | Mallo et al. |
| 2002/0127257 A1 | 9/2002 | Gers-Barlag et al. |
| 2002/0146375 A1 | 10/2002 | Schreiber et al. |
| 2002/0193544 A1 | 12/2002 | Loffler et al. |
| 2003/0087789 A1 | 5/2003 | Scheffler |
| 2003/0211061 A1 | 11/2003 | Deckner et al. |
| 2004/0042994 A1 | 3/2004 | Dausch et al. |
| 2004/0063886 A1 | 4/2004 | Loffler et al. |
| 2004/0213819 A1 | 10/2004 | Albrecht |
| 2004/0265243 A1 | 12/2004 | Albrecht et al. |
| 2005/0013833 A1 | 1/2005 | Simonnet |
| 2005/0048009 A1 | 3/2005 | Goppel et al. |
| 2005/0053634 A1 | 3/2005 | Ruppert et al. |
| 2005/0074414 A1 | 4/2005 | Tamarkin et al. |
| 2005/0165188 A1 | 7/2005 | Loffler et al. |
| 2005/0266055 A1 | 12/2005 | Stiller et al. |
| 2006/0029657 A1 | 2/2006 | Popp et al. |
| 2006/0057075 A1 | 3/2006 | Arkin et al. |
| 2006/0093571 A1 | 5/2006 | Glinski |
| 2006/0135383 A1 | 6/2006 | Cossa et al. |
| 2006/0159637 A1 | 7/2006 | Meyer et al. |
| 2007/0065381 A1 | 3/2007 | Elsbrock et al. |
| 2007/0209552 A1 | 9/2007 | Gottschalk-Gaudig |
| 2007/0231418 A1 | 10/2007 | Scheffler |
| 2007/0299285 A1 | 12/2007 | Scheffler |
| 2009/0068257 A1 | 3/2009 | Leunis et al. |
| 2010/0179219 A1 | 7/2010 | Meyer |
| 2010/0189662 A1 | 7/2010 | Neubourg |
| 2010/0278763 A1* | 11/2010 | Loeffler et al. ............ 424/59 |
| 2010/0316684 A1 | 12/2010 | Daniels |
| 2012/0315315 A1 | 12/2012 | Neubourg |
| 2014/0050790 A1 | 2/2014 | Scheffler |

FOREIGN PATENT DOCUMENTS

| | | | |
|---|---|---|---|
| CN | 1426305 A | | 6/2003 |
| CN | 101080212 A | | 11/2007 |
| DE | 3 330 628 A1 | | 3/1985 |
| DE | 4 431 365 A1 | | 3/1995 |
| DE | 19825961 | | 12/1999 |
| DE | 19907715 | | 8/2000 |
| DE | 199 23 648 | | 11/2000 |
| DE | 10162840 | | 7/2003 |
| DE | 102004039212 A1 | | 3/2006 |
| DE | 198 25 961 B4 | | 4/2006 |
| EP | 0 194 097 A1 | | 9/1986 |
| EP | 0 257 336 A2 | | 3/1988 |
| EP | 0 268 164 A2 | | 5/1988 |
| EP | 0 598 412 A2 | | 5/1994 |
| EP | 0835647 | | 4/1998 |
| EP | 0 956 851 A1 | | 11/1999 |
| EP | 1069142 | | 1/2001 |
| EP | 1 108 421 A1 | | 6/2001 |
| EP | 1116733 | | 7/2001 |
| EP | 1138703 | | 10/2001 |
| EP | 1046387 | | 2/2002 |
| EP | 1352639 | | 10/2003 |
| EP | 1 410 790 A1 | | 4/2004 |
| EP | 1 852 105 A2 | | 11/2004 |
| EP | 1 000 874 B1 | | 12/2005 |
| EP | 1 323 410 B1 | | 9/2006 |
| EP | 1 758 555 B1 | | 2/2009 |
| EP | 2 335 675 A1 | | 6/2011 |
| FR | 2217405 A1 | | 9/1974 |
| FR | 2 802 805 A | | 6/2001 |
| FR | 2 825 629 A | | 12/2002 |
| GB | 2282385 A | | 4/1995 |
| JP | S51-12591 B1 | | 4/1976 |
| JP | S57-42326 A | | 3/1982 |
| JP | H09-143023 A | | 6/1997 |
| JP | 1998-114619 | | 5/1998 |
| JP | 2000-038336 A | | 2/2000 |
| JP | 2000-505829 A | | 5/2000 |
| JP | 2003-206222 A | | 7/2003 |
| JP | 2004-514000 | | 5/2004 |
| JP | 2004-331610 A | | 11/2004 |
| JP | 2005-002030 A | | 1/2005 |
| JP | 2006-069912 | | 3/2006 |
| JP | 2007-008853 A | | 1/2007 |
| JP | 2010-500983 A | | 1/2010 |
| WO | 94/09829 A1 | | 5/1994 |
| WO | 96/27376 A1 | | 9/1996 |
| WO | 98/56333 A1 | | 12/1998 |
| WO | 00/15193 A1 | | 3/2000 |
| WO | 00/62751 A2 | | 10/2000 |
| WO | 01/62222 A2 | | 8/2001 |
| WO | 01/72315 A1 | | 10/2001 |
| WO | 02/085921 A2 | | 10/2002 |
| WO | 03/017968 A2 | | 3/2003 |
| WO | WO 03/022236 | | 3/2003 |
| WO | 03/026603 A2 | | 4/2003 |
| WO | 03/049715 A2 | | 6/2003 |
| WO | 2004/016336 A1 | | 2/2004 |
| WO | WO 2004/017930 | | 3/2004 |
| WO | 2004/060063 A1 | | 7/2004 |
| WO | 2005/076697 A2 | | 8/2005 |
| WO | 2005/080451 A1 | | 9/2005 |
| WO | 2005/097069 A1 | | 10/2005 |
| WO | 2005/123037 A1 | | 12/2005 |
| WO | 2006/003981 A1 | | 1/2006 |
| WO | 2006/044193 A2 | | 4/2006 |
| WO | WO 2006/065530 | | 6/2006 |
| WO | 2006/110555 A2 | | 10/2006 |
| WO | 2007/052230 A1 | | 5/2007 |
| WO | 2008/086953 A1 | | 7/2008 |
| WO | WO 2008/087326 | | 7/2008 |
| WO | WO 2008/138894 | | 11/2008 |
| WO | WO 2008/155389 | | 12/2008 |
| WO | WO2009/083130 | * | 7/2009 ............ C08F 220/58 |
| WO | 2010/060896 A1 | | 6/2010 |
| WO | 2010/096868 A1 | | 9/2010 |
| WO | 2011/071629 A1 | | 6/2011 |
| WO | 2011/107522 A2 | | 9/2011 |

OTHER PUBLICATIONS

Anonym, "Taking care of your sensory innovations, Aristoflex AVC and Aristoflex HMB" 2003.
"A story about aerosol," Japan Association of Aerosol Science and Technology http://www.jaast.jp/hanashi/, downloaded Jun. 10, 2013 (2 pgs).
"Aerosol" *Wikipedia*, http://en.wikipedia.org/w/index.php?title=Aerosol&printable=yes, 11 pages, Downloaded Dec. 10, 2013.
"caprylic acid—Compound Summary," National Center for Biotechnology Information, PubChem Compound Database, http://pubchem.ncbi.nlrn.nih.gov/summary/summary.cgi?cid=379 &loc=ec rcs; downloaded Sep. 24, 2012 (10 pgs.).
"Cosmetic Science," Verlag Asakura, Japan, mhtml:http://svapdb04/NvClientDownload/ViewTemp/ka0003/20140312141947.mht, downloaded on Mar. 12, 2014 (3 pgs.).
"decanoic acid—Compound Summary," National Center for Biotechnology Information PubChem Compound Database, http://pubchem.ncbi.nlm.nih.gov/summary/summary.cgi?cid=2969, downloaded Sep. 24, 2012 (10 pgs.).
"Defoamer" *Wikipedia*, http://en.wikipedia.org/wiki/Defoamer (last modified on Dec. 22, 2013) 5 pgs.
"Dispersion (chemistry)" *Wikipedia*. http://en.wikipedia.org/w/index.php?title=Dispersion_(chemistry)&printable=yes, 3 pages, Downloaded Dec. 10, 2013.

(56) References Cited

OTHER PUBLICATIONS

"Emulsion," Wikipedia http://de.wikipedia.org/w/index.php?title=Emulsion&printable=yes, Printed Apr. 3, 2014.
"Equisetum," *Wikipedia*, http://en.wikipedia.org/w/index.php?title=Equisetum&oldid 630458996, last updated: Oct. 21, 2014 (4 pages).
"How Aerosol Cans Work" *HowStuffWorks*. http://science.howstuffworks.com/innovation/everyday~innovations/aerosol-can3.htm, 1 page downloaded Dec. 10, 2013.
"Hydrogenated lecithin," Environmental Working Group's Skin Deep® Cosmetics Database, downloaded Jul. 16, 2012 (www.ewg.org).
"Ionic polymerization," *Wikipedia* http://en.wikipedia.org/w/index.php?title=ionic_polymerization&printable=yes, [retrieved on Mar. 5, 2014], 4 pages.
"Ionomer," *Wikipedia*, http://en.wikipedia.org/w/index.php?tille=ionomer&printable=yes, [retrieved on Mar. 5, 2014], 3 pages.
"Key Attributes of TKDL (Traditional Knowledge Digital Library): Zimaad-e-Dibq," Exhibit 1 in 3$^{rd}$ Party Observations filed May 27, 2014 in European Patent No. 11705632.5 (2 pages).
"Key Attributes of TKDL (Traditional Knowledge Digital Library): Zimaad Barae Awraam-e-zahira," Exhibit 2 in 3$^{rd}$ Party Observations filed May 27, 2014 in European Patent No. 11705632.5 (2 pages).
"Key Attributes of TKDL (Traditional Knowledge Digital Library): Zimaad-e-lklil-ul-Jabal," Exhibit 3 in 3$^{rd}$ Party Observations filed May 27, 2014 in European Patent No. 11705632.5 (2 pages).
"Key Attributes of TKDL (Traditional Knowledge Digital Library): Mahatrnakatailam," Exhibit 4 in 3$^{rd}$ Party Observations filed May 27, 2014 in European Patent No. 11705632.5 (9 pages).
"Key Attributes of TKDL (Traditional Knowledge Digital Library): Manusa Bola Gunah," Exhibit 5 in 3$^{rd}$ Party Observations filed May 27, 2014 in European Patent No. 11705632.5 (2 pages).
"Key Attributes of TKDL (Traditional Knowledge Digital Library): Zaroor Aseequlaan," Exhibit 6 in 3$^{rd}$ Party Observations filed May 27, 2014 in European Patent No. 11705632.5 (3 pages).
"Lecithin—The importance of phospholipid terminology," *INFORM*, vol. 7, No. 11, p. 1168 (1996).
"Lecithin," Environmental Working Group's Skin Deep® Cosmetics Database, downloaded Jul. 16, 2012 (www.ewg.org).
"Multi-Lamellar Emulsion," Wikipedia, http://en.wikipedia.org/windex.php?title=Multi-Lamellar_Emulsion&printable-yes Lasr updated: Nov. 4, 2011; downloaded Sep. 4, 2014 (2 pgs.).
"Obviously arranged" Patent-Google Search, https://www.google.de/search?sourceid=ie7&q=%22obviously+arranged%22+ep&rls . . . (1 page), Printed Feb. 28, 2014.
"Pentylene Glycol," Environmental Working Group's Skin Deep® Cosmetics Database, downloaded Jul. 16, 2012 (www.ewg.org).
"Pickering Emulsion," Wikipedia, 1 page (Jul. 29, 2013).
"Propylene Glycol," Environmental Working Group's Skin Deep® Cosmetics Database, downloaded Jul. 16, 2012 (www.ewg.org).
"Surface-active agents," *Römpp Chemie Lexikon*, 9$^{th}$ Edition, Prof. Jürgen Falbe and Prof. Manfred Regitz, Editors, Georg Thieme Verlag, Stuttgart, pp. 1649-1650 (1993).
"Tagespfiege Day Cream, Optolind", Mintel Group Ltd., Global New Product Database (GNPD), URL, http://www.gnpd.com/sinatra/gnpd/search_results&search_id=Wt6LladEma/&p_page_number=2&item_id=140346, downloaded Jul. 5, 2013.
"Usnea," *Wikipedia*, http://en.wikipedia.org/w/index.php?title=Usnea&oldid=625407500, last updated: Sep. 13, 2014 (5 pages).
"What is the Meaning of the Term "Emulsifier-free"?" Definition by the Society for Dermopharmacy, *DermoTopics*, Issue 1 (2003), (http://www.dermotopics.de/german/ausgabe—1_03_d/emulgatorfrei_1_2003_d.htm) retrieved Mar. 14, 2016.
Abe et al., "Ursolic Acid as a Trypanocidal Constituent in Rosemary," *Biol Pharm Bull* 25(11):1485-1487 (2002).
Abram et al., "Mousses," *Handbook of Cosmetic Science and Technology*, (Barel, A.O.; Paye, Marc; Maibach, Howard I.) p. 221-232 (2001).
A-Clear Foam Cream, http://www.gowoonus.com/skgiciearingfoacreamer.aspx, Downloaded Mar. 12, 2014 (1 page).
Ansmann, "Cosmetic emulsions: stabilizing mechanisms with the help of modern analytical and physico-chemical measurements," *Skin Care Forum*, Issue 39 (2005).
Binks et al., "Aqueous foams stabilized solely by silica nanoparticles," *Agnew Chem* 117, pp. 3788-3791 (2005).
Brandl et al., "Morphology of semisolid aqueous phosphatidylcholine dispersions, a freeze fracture electron microscopy study," *Chemistry and Physics of Lipids*, 87, pp. 65-72 (1997).
Brandl et al., "Preparation and characterization of semi-solid phospholipid dispersions and dilutions thereof," *International Journal of Pharmaceutics*, 170, pp. 187-199 (1998).
Brandl et al., "Three-dimensional liposome networks: freeze fracture electron microscopical evaluation of their structure and in vitro analysis of release of hydrophilic markers," *Advanced Drug Delivery Reviews* 24, pp. 161-164 (1997).
Brandl, "Liposomes as drug carriers: a technological approach," *Biotechnology Annual Review*, vol. 7, pp. 59-85 (2001).
Carr, "Tea Trees and Their Therapeutic Properties," *The Linus Pauling Institute*, Oregon State University, Fall/Winter 1998 (4 pgs.).
Daniels et al., "Skin care: Betulin for surfactant-free emulsions," *Pharmazeutische Zeitung*, 153(11):34-35 (2008).
Daniels, "Die richtige Galenik für kranke Haut," (Translation, "The Right Galenics for Diseased Skin"), *Dermopharmacy* (2009).
Daniels, "Galenic principles of modern skin care products", *Skin Care Forum* (25) (2001).
Daniels, "Lamellare System—an overview," Presentation at Koko Company Seminar/Universität Tubingen, Berlin, Mar. 3, 2012 (15 pages).
Daniels, "Manufacturing protocol for reworking Example 1 of US 2006-0029657," Apr. 10, 2013 (5 pgs.).
Eurosurface—Anest Iwata Europe—Accessories—PC 18 D Pressurized Container, http://www.anest-iwataeu.com/products.asp?Lin=7&Prod=168, retrieved from the internet on Dec. 3, 2014 (1 page).
Foam Cream Aloe/Olive 150 ml, http://www.raue-shop.de/en/camillen-60/wellness-fusspftege/aloe-olive/pftegeschaum, retrieved from the internet on Dec. 3, 2014 (1 page).
Galgon et al., "Identification and Quantification of Betulinic Acid," *Phytochemical Analysis*; 10:187-190 (1999).
Glombitza et al., "Influence of different ceramides on the structure of in vitro model lipid system of the stratum corneum lipid matrix," *Chemistry and Physics of Lipids*, 117, pp. 29-44 (2002).
*Grundlagen der Arzneiformlehre (Fundamentals of Drug Morphology), Galenik 2*, Herzfeldt et al. (eds.), Springer Publishing (1999)—Product Flyer only.
Hayek et al., "A bicentennial of Betulin,"*Phytochemistry* 28(9):2229-2242 (1989).
Hoepfner et al., *Fiedler—Lexikon der Hilfsstoffe: Für Pharmazie, Kosmetik und angrenzende Gebiete* (Fiedler—Encyclopedia of Excipients for pharmaceuticals, cosmetics and related fields), 5th edition, Editio Cantor, Verlag Aulendorf, pp. 97-121 (2001).
Huyke et al., "Treatment of actinic keratoses with birch bark extract: a pilot study," *Journal der Deutschen Dermatologischen Gesellschaft (JDDG)*, 4(2):132-136 (2006).
IBIDAPO, "Classification of ionic polymers," *Polymer Engineering & Science*, vol. 28, Issue 22, pp. 1473-1476 (1988) http://onlinelibrary.wiley.com/doi/10.1002/pen.760282207/abstract, [retrieved on Feb. 28, 2014].
Israelachvili, "Aggregation of Amphiphilic Molecules Into Micelles, Bilayers, Vesicles and Biological Membranes " *Intermolecular & Surface Forces, Second Edition*, Academic Press, London, UK, Chapter 17, pp. 366-394 (1992).
Jager et al., "Solubility studies of oleanoic acid and betulinic acid in aqueous solutions and plant extracts of Viscum album L.", Planta Med, 73:157-162 (2007).

(56) References Cited

OTHER PUBLICATIONS

Klein, "Choosing Thickening Agents for Emulsions, Part I: Water Phase Thickeners," *Cosmetics & Toiletries*, vol. 118, No. 2, pp. 42-46 (2003).
Laszczyk et al., "Physical, chemical and pharmacological characterization of a new oleogelforming triterpene extrac' from the outer bark of birch (Betulae Cortex)", Planta medica, 72(15):1389-1395 (2006).
Laszczyk, M., "Triterpentrockenextrakt aus Birkenkork (Betula alba cortex), Untersuchungen zur chemischen Zusammensetzung, Galenik, Penetration und pharmakologisch-biologischen Wirkung" ("Triterpene dry extract of the outer bark of birch (Betula alba cortex) Investigations of its chemical composition, galenic possibilities, penetration and pharmacological-biological effects"), Ph.D. thesis, chapters 3.7 and 3.8, Albert-Ludwigs-University, Freiburg, Germany (2007) Abstract and relevant chapters.
*Latices and Pseudolatices in Modern Pharmaceutics*, Fourth Edition, G.S. Banker, J. Siepmann, and Cgr. Rhodes, Editors, p. 412 (2006).
Lautenschlager, "Universal base creams with membrane structure for skin care, skin protection and dermatics," *Österreichische Apothekerzeitung*, 56(14):679 (2002).
Manufacturer Specification Aromtech: Arctic Birch Bark Extract (2009).
Manufacturer Specifications RITALAB: White Birch Bark Extract P INCI Name: Betula Alba Bark Extract (Jun. 6, 2008).
Mehnert et al., "Solid lipid nanoparticles: Production, characterization and applications," Advanced Delivery Reviews 47, pp. 165-196 (2001).
Menner et al., High internal phase emulsion templates solely stabilised by functionalized titania nanoparticles, *ChemComm*, 9th, (Aug. 2007).
Menner et al., "Particle-Stabilized Surfactant-free Medium Internal Phase Emulsions as Templates for Porous Nanocomposite Materials: poly-Pickering foams," *Langmuir* 23, pp. 2398-2403 (2007).
Muller-Goymann, Photographs "TEM-Aufnahme und Polarisationsmikroskopie einer Lamellarphase," *Pharmazeutische Technologie* (2013) 1 pg.
Myers, *Surfaces, Interfaces, and Colloids: Principles and Applications*, Second Edition, John Wiley & Sons (1999).
New, "Antileishmanial activity of amphotericin and other antifungal agents entrapped in liposomes," *J. Antimicrob. Chemother.* 8:371-381, Oxford University Press, London, England (1981).
Paulke, "Kapitel 1.8., Polymere Nanopartikel—Latex/Pseudolatex, Emulsionspolymerisation and pharmazeutische Anwendungen," Fraunhofer Institute for Applied Polymer Research, Potsdam-Golm, Germany, 7 pages.
Raab et al., "Pfiepekosmetik: Ein Leitfaden" (Care Cosmetics: A Guide) 4th Edition, Wissenschaftliche Verlagsgesellschaft mbH, Stuttgart, pp. 151-159, (2004).
Reiger, "Nonionic Surfactants " *Cosmetics & Toiletries, Surfactant Encyclopedia*, 2nd Edition, Chapter IV, pp. 24-36 (1996).
Schneider, "Lecithine—Gewinnung, Eigenschaften and Bedeutung fur die industrielle Anwendung", *Fat Sci Technol.*, vol. 94, pp. 524-533 (1992).
Schöffling, "Emulgatorfreie Emulsionen," *Galenics* (2009) (Translation, "Emulsifier-Free Emulsions, Microfine Particles Replace Emulsifiers").
Scholfield, "Composition of Soybean Lecithin", *Journal of the American Oil Chemists' Society*, vol. 58, No. 10, pp. 889-892 (1981).
Schuchmann et al., "Emulgieren: Mehr als nur Zerkleinern," *Chemie Ingenieur Technik* 76, No. 4, (2004) (12 pages).
Schuchmann, "Tropfenaufbruch beim mechanischen Emulgieren," Karlsruher Institut für Technologie (KIT); Hochschulkurs Emulgiertechnik (2012).
Shah et al., "Interaction of Calcium Ions with Lecithin and Sphingomyelin Monolayers," *Lipids* 2(1):21-27, American Oil Chemists' Society, Springer, Germany (1967).
Shchipunov et al.: "Phase Behavior of Lecithin at the Oil/Water Interface", *Langmuir*, vol. 12, No. 26, pp. 6443-6445 (1996).
Stegmeyer, "Lytrope Flussigkristalle: Grundlagen, Entwicklung, Andwendung," (Lyotropic Liquid Crystals: Basics, Development, Application), Chapter 5.2.2.2—Ointments and Creams (1 pg), Publisher: Darmstadt Steinkopff (1999).
Steifel® Research Australia, "Physiogel foam investigation II," 5 pg. (Mar. 27, 2014).
Stoye, "Permeabilitäts veränderung von humanem Stratum corneum nach applikation nicht-steroidaler Antirheumatika in verschiedenen kolloidalen Tragersystemen," ("Permeability changes of human stratum corneum by application of non-steroidal anti-inflammatory drugs in various colloidal carrier systems") Dissertation thesis, 89 pgs. (1997) Relevant portions.
Surface Active Agents, http://old.iupac.org/reports/2001/colloid_2001_/manual_of_s_and_l/node36.html, retrieved from the internet on Dec. 3, 2014 (2 pgs.).
The Free Dictionary, Definition of active agent, http://www.thefreedictionary.com/active+agent, retrieved from the internet on Dec. 3, 2014 (1 page).
The Free Dictionary, Definition of surface active, http://www.thefreedictionary.com/surface-active, retrieved from the internet on Dec. 3, 2014 (1 page).
The Free Online Encyclopedia, Definition of bulk solid, http://encyclopedia2.thefreedictionary.com/bulk+solid, retrieved from the internet on Dec. 3, 2014 (1 page).
The Free Online Encyclopedia, Definition of particulate solid, http://encyclopedia2.thefreedictionary.com/particulate+solid, retrieved from the internet on Dec. 3, 2014 (1 page).
Vortragszusammenfassung Firmenseminar 2, (Presentation Summaries, Company Seminar 2, "Betulin for the Skin—New Information on Galenics, Application, and Effects,") 13th Annual Meeting of the Society of Dermopharmacy, Heidelberg, Germany (Mar. 31, 2009).
Wohlrab et al., "Interaction of Epicutaneously Applied Lipids with Stratum Corneum Depends on the Presence of either Emulsifiers or Hydrogenated Phosphatidylcholine," *Skin Pharrnacol Physiol* 23, pp. 298-305 (2010).
European Patent Office, International Search Report in International Application No. PCT/EP2010/007542 (Mar. 2, 2011).
European Patent Office, Written Opinion in International Application No. PCT/EP2010/007542 (Mar. 2, 2011).
European Patent Office, International Preliminary Report on Patentability in International Application No. PCT/EP2010/007542 (Jun. 12, 2012).
State Intellectual Property Office of People'S Republic of China, Notification of Reexamination in Chinese Patent Application No. 201080055599.9 (Mar. 7, 2016).

* cited by examiner

EMULSIFIER-FREE, POLYMER-STABILIZED FOAM FORMULATIONS

This is a 371 of PCT/EP10/007542 filed Dec. 10, 2010, claiming benefit of U.S. provisional application No. 61/285,252, filed Dec. 10, 2009, and the priority of European number 09015330.5 filed Dec. 10, 2009, hereby incorporated by reference.

TECHNICAL FIELD OF THE INVENTION

The present invention relates to cosmetic and dermatological foam formulations, particularly to foam creams, based on emulsions of the oil-in-water type, which are free or substantially free of conventional emulsifiers and which comprise at least one surface active, ionic polymer with a molecular weight of more than 5000 g/mol, wherein the ionic polymer is a copolymer comprising as monomer units an ionic monomer and at least one further monomer.

BACKGROUND OF THE INVENTION

1. Emulsions

Generally, the term "emulsion" relates to heterogeneous systems consisting of two liquids that are not miscible or only miscible to a limited extent, which are typically designated as phases. In an emulsion, one of the two liquids is dispersed in the other liquid in the form of minute droplets.

In case that the two liquids are water and oil and in case the oil droplets are finely dispersed in water, the emulsion is an oil-in-water emulsion (O/W-emulsion, e.g. milk). The basic character of an O/W-emulsion is defined by the water. In case of a water-in-oil emulsion (W/O-emulsion, e.g. butter) the opposite principle applies, wherein the basic character is in this case defined by the oil.

In order to obtain a durable dispersion of a liquid in another liquid, emulsions in a conventional sense require the addition of a surface active agent (emulsifier). Emulsifiers have an amphiphilic molecular structure consisting of a polar (hydrophilic) and a non-polar (lipophilic) part of the molecule, which are spatially separated from each other. In simple emulsions, one of the phases contains finely dispersed droplets of the second phase, which are enclosed by an emulsifier shell (water droplets in W/O-emulsions or lipid vesicles in O/W-emulsions). Emulsifiers reduce the surface tension between the phases by being arranged at the interface between the two liquids. They form interfacial films at the oil/water phase interface which countervails the irreversible coalescence of the droplets. For stabilizing emulsions, mixtures of emulsifiers are often used.

The term "emulsifier" or "conventional emulsifier" is known in the art. Conventional emulsifiers and their use are described, e.g., in the publications: Pflegekosmetik, 4th edition, Wissenschaftliche Verlagsgesellschaft mbH Stuttgart, pages 151 to 159, and Fiedler Lexikon der Hilfsstoffe, 5th edition, Editio Cantor Verlag Aulendorf, pages 97 to 121.

Conventional emulsifiers can be classified, based on the hydrophilic part of the molecule, into ionic (anionic, cationic and amphoteric) emulsifiers and non-ionic emulsifiers:

The probably best known example of an anionic emulsifier is soap which is the conventional name for water-soluble sodium or potassium salts of saturated and unsaturated higher fatty acids.

Important members of cationic emulsifiers are quaternary ammonium compounds.

The hydrophilic part of the molecule of non-ionic emulsifiers often consists of glycerol, polyglycerol, sorbitans, carbohydrates or polyoxyethylene glycols, and is most often connected by means of ester and ether bonds to the lipophilic part of the molecule. The latter typically consists of fatty alcohols, fatty acids or iso-fatty acids.

By variation of the structure and the size of the polar and the non-polar part of the molecule, lipophilicity and hydrophilicity of emulsifiers may be modified to a large extent.

The correct choice of the emulsifiers is decisive for the stability of an emulsion. In this respect, the characteristics of all substances contained in the system need to be considered. In case of skin care emulsions, for example, polar oil components such as e.g. UV filters may cause instabilities. Therefore, besides emulsifiers, other stabilizers are additionally used, which, e.g. increase the viscosity of the emulsion and/or act as protective colloid.

Emulsions represent an important type of product in the field of cosmetic and/or dermatological preparations, which is used in different areas of application. Accordingly, a range of products—such as lotions and creams—are available for skin care, particularly for relubricating dry skin. The aim of skin care is to compensate the loss of lipid and water caused by daily washing. In addition, skin care products should protect from environmental stress—in particular from sun and wind—and delay skin aging.

Cosmetic emulsions are also used as deodorants. Such formulations serve for eliminating the odour of the body that is formed when fresh sweat, that as such is free of odour, is decomposed by microorganisms.

Emulsions in the form of cleaning emulsions are also used for the cleaning of the skin and skin adnexa. They are most often used for the cleaning of the face and especially for removing decorative cosmetics. Such cleaning emulsions have the advantage—in contrast to other cleaning preparations such as soap—to be particularly skin compatible since they may contain in their lipophilic phase nurturing oils and/or non-polar active agents—such as, e.g., vitamin E.

2. Emulsifier-Free Emulsions

The IUPAC defines the term "emulsifier" as follows: Emulsifiers are surface active substances. They are preferably arranged in the interface between oil phase and water phase, and thereby reduce the surface tension. Even in low concentration, emulsifiers facilitate the formation of an emulsion. Moreover, these substances are able to enhance the stability of emulsions by reducing the rate of aggregation and/or coalescence.

For stabilizing pharmaceutical and cosmetic emulsions, mainly so-called genuine emulsifiers (i.e. conventional emulsifiers in the sense of the present description) are used, that according to their structure and their physico-chemical behaviour belong to the class of surfactants. They are characterized by an amphiphilic structure and the capability of micelle association.

Such low molecular, amphiphilic substances are, however, repeatedly cited as the cause of incompatibilities of skin care products, such as e.g. a disfunction of the skin barrier or Mallorca acne. Therefore, the cosmetics industry is looking for alternatives to the conventional formulations in the form of emulsifier-free emulsions.

Emulsifier-free emulsions are free of conventional emulsifiers, i.e. amphiphilic substances having a low molecular weight (i.e. molecular weight <5000 g/mol), that, in suitable concentrations, can form micelles and/or other liquid crystalline aggregates.

The term "emulsifier-free" is established in the art. According to a definition of the Society for Dermopharmacy, which was adopted by an interdisciplinary consent among pharmacists, dermatologists and other experts (http://www-.dermotopics.de/german/ausgabe_1_03_d/emulgatothei_1_2003_d.htm), a formulation can be designated as "emulsifier-free" when it is stabilized by means of surface active macromolecules (molecular weight of above 5000 g/mol) instead of by emulsifiers in a narrower sense (i.e. conventional emulsifiers).

The use of polymeric and solid emulsifiers has proved to be a promising approach for emulsifier-free emulsions with the goal of obtaining sufficiently stable and cosmetically attractive products, which help to avoid the disadvantages connected with conventional emulsifiers.

3. Solid-Stabilized Emulsions

An example of emulsifier-free emulsions are emulsions stabilized by solids. Solid-stabilized emulsions, which are known in the art as Pickering emulsions, are stabilized by means of finely dispersed solid particles and, as far as possible, allow for the abdication of conventional emulsifiers.

In solid-stabilized emulsions, solids accumulate at the oil/water phase interface in the form of a layer whereby the coalescence of the dispersed phase is prevented.

Suitable solid emulsifiers are in particular particulate, inorganic or organic solids, which are wettable by both hydrophilic and lipophilic liquids. Preferably, in the solid-stabilized emulsions or Pickering emulsions, e.g. titanium dioxide, zinc oxide, silicon dioxide, $Fe_2O_3$, veegum, bentonite or ethyl cellulose are used as solid emulsifiers.

4. Polymer-Stabilized Emulsions

A further example of emulsifier-free emulsions are polymer-stabilized emulsions. In the case of polymer-stabilized emulsions and in contrast to the conventional emulsions, the required stabilization is not achieved by amphiphilic, surfactant-like emulsifiers, but by means of suitable macromolecules. The irritation potential of formulations that are stabilized in this way differs significantly from that of emulsions which are stabilized by conventional emulsifiers. Due to their high molecular mass, polymeric emulsifiers cannot penetrate into the stratum corneum. Therefore, undesired interactions, e.g. in the sense of Mallorca acne, are not to be expected.

If polymers are added, their stabilizing effect is often due to their thickening effect and due to a flow boundary provided to the outer phase of the emulsion.

The use of surface active macromolecules, such as carbomer 1342 or hydroxypropyl methyl cellulose as primary emulsifiers is substantially more effective. These macromolecules form structured interfacial films that ensure an effective protection against coalescence. In this case, the increase of viscosity of the outer phase is of minor importance for the stability of the emulsions.

The structure of the interfacial film formed by polymeric emulsifiers can be generally described by the so-called tail-loop-train-model (see Myers D., Polymers at Interfaces, in Meyers D.: Surfaces, interfaces and colloids. VHC Publishers New York, pages 283-297, 1991), which is depicted schematically in FIG. 1.

Polymers can be used as emulsifiers in case they exhibit a sufficiently high surface activity. Copolymers with a high molecular weight which contain, in addition to a hydrophilic monomer portion, a monomer portion with a lower polarity, are particularly suitable. Besides an increase in viscosity in the continuous water phase, they cause simultaneously and mainly a stabilization of the oil/water phase interface. The portion having a lower polarity adsorbs to the oil phase and the hydrophilic structure swells in the aqueous phase to form a gel structure at the phase interface. The gel structure formed by the strongly hydrated, hydrophilic polymer segments, e.g. in the form of minute gel droplets along the oil/water phase interface, may provide an even more effective protection against coalescence than a non-gel-like interfacial film, as formed e.g. by hydroxypropyl methyl cellulose.

The exact molecular arrangement of the copolymeric emulsifiers at the phase interface is significantly determined by the distribution of the hydrophilic and the less polar segments in the overall copolymer molecule. In FIG. 2, possible arrangements are depicted schematically for A-B-block copolymers [FIG. 2, (A)], A-B-A-block copolymers [FIG. 2, (B)], and for copolymers having a random distribution of hydrophilic segments and segments of lower polarity [FIG. 2, (C)].

Without wanting to be bound to any theory, it is assumed that a particularly good stabilization of the emulsions can be achieved especially by cross-linked, ionic copolymers. This is due to the fact that the cross-linkage prevents a strong unfolding of the hydrophilic (ionic) polymer segments in the aqueous phase. Accordingly, the hydrophilic (ionic) polymer segment cannot arbitrarily spread out in the aqueous phase, but retains a compact structure and must hydrate and swell next to the oil/water phase interface. As a result thereof, a particularly rigid, droplet-like gel structure is formed at the oil/water phase interface which provides an optimal protection against coalescence and an optimal stabilizing effect.

A stabilization of oil-in-water emulsions by formation of the described gel structure at the oil/water phase interface is effected for example by the polymeric emulsifier Carbomer 1342. Carbomer 1342 is a copolymer of acrylic acid and $C_{10}$-$C_{30}$ alkyl acrylates, wherein the hydrophilic acrylic acid portion prevails the lipophilic alkyl acrylate portion. The $C_{10}$-$C_{30}$ alkyl acrylates are additionally cross-linked by allyl pentaerithrol.

Particularly effective stabilizers for emulsifier-free oil-in-water emulsions are the diverse, commercially available copolymers of 2-acrylamido-2-methylpropane sulfonic acid. 2-acrylamido-2-methylpropane sulfonic acid having the chemical formula (2)

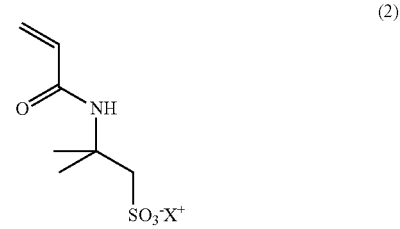

(2)

wherein $X^+$ is $H^+$ in the case of the free acid, is also called AMPS or 2-methyl-2-[(1-oxo-2-propenyl)amino]-1-propanesulfonic acid. Its salts (wherein $X^+$ represents a cation other than $H^+$) are also called acryloyl dimethyltaurates.

To this family of particularly suitable copolymers belong the commercially available polymers Aristoflex® AVC and Aristoflex® HMB of the company Clariant. Aristoflex® AVC (INCI name ammonium acryloyldimethyltaurate/vinylpyrrolidone copolymer) and Aristoflex® HMB (INCI name ammonium acryloyldimethyltaurate/beheneth-25 methacrylate crosspolymer) comprise an ionic monomer portion, 2-acrylamido-2-methylpropane sulfonic acid (AMPS), as well as a further, less polar monomer portion (vinylpyrrolidone or beheneth-25 methacrylate). These polymers are used as thickener and as stabilizer for oil-in-water emulsions and form extremely stable emulsions already at low concentrations. In particular, these polymers can be used in conjunction with almost any oil phase, comprising silicone oils, hydrocarbons/waxes and ester oils. Furthermore, they can be used over a wide pH range (Aristoflex® AVC: pH 4.0 to 9.0; Aristoflex® HMB: pH 3.0 to 9.0), and they are UV stable.

Copolymers of 2-acrylamido-2-methylpropane sulfonic acid are also offered and developed by the company Seppic as polymeric emulsifiers for emulsifier-free emulsions. Amongst those are the commercially available product Sepinov™ EMT 10 (INCI name hydroxyethyl acrylate/sodium acryloyldimethyltaurate copolymer, CAS-number 111286-86-3), as well as the experimental polymers 8732MP (product name: Sepinov P88, a sodium acrylate/acryloyldimethyltaurate/dimethylacrylamide crosspolymer, CAS-number 187725-30-0), 8885MP2 (product name: Sepinov EG-P, a sodium acrylate/sodium acryloyldimethyltaurate copolymer, CAS-number 77019-71-7), and 8947MP. These polymers also have good emulsifying properties, are usable over a wide pH range (e.g. for Sepinov™ EMT 10 pH 3-11), and are UV stable.

Aristoflex® AVC, Aristoflex® HMB, Sepinov™ EMT 10 and the experimental Seppic-polymers 8732MP, 8885MP2 and 8947 MP are formulated in an already neutralized form, i.e. the 2-acrylamido-2-methylpropane sulfonic acid unit is present in the formulation at least partially as a salt, and they are in powder form.

Acryloyldimethyltaurate copolymers, their manufacture, and their use as thickeners or stabilizers of emulsions for cosmetic and pharmaceutical applications are described for example in the publications EP 1 069 142 A1, EP 1 116 733 A1, WO 2008/087326 A2 and EP 1 138 703 A1.

WO 03/022236 A1 describes the use of taurate copolymers, and in particular of Aristoflex® AVC, as thickener and stabilizer for cosmetic compositions, in particular for lotions and cream formulations, comprising $C_1$-$C_{25}$ alpha- or beta-hydroxycarboxylic acids.

5. Foam Formulations

A particular application form of cosmetic and/or dermatological emulsions is the application as foams. Foam formulations have the advantage that they can be easily distributed on the skin. The foamy consistency is experienced as comfortable and the products normally leave a good skin feeling. In particular, the physical structure of the foam acts positively on the protective function of the skin. Foams are complicated physical structures that require a particular adjustment of the components constituting the foam. In general, foams are obtained by spraying an emulsion formulation or an aqueous surfactant (stabilizer) solution. For example, an emulsion charged with a propellant is dispensed from a pressurized container (in the literature and the patent literature such systems are also called aerosol foams). The pressurized mixture of emulsion and propellant expands and forms the foam bubbles. In particular, the dispersed oil phase, in which the oil-soluble gas is dissolved, expands. However, foams can also be formed by means of other systems such as, for example, pump sprays.

Upon application, balanced foam formulations have a stable two-phase or multi-phase, polydisperse structure that forms on the skin a network structure which is comparable to a membrane. Such network structures have the advantage that they develop a protective action, for example against contact with water, however, allow for the unhindered gas exchange with the environment. In such foams, there is practically no obstacle for the perspiratio insensibiles and no corresponding heat build-up. Thereby, the positive properties of a protective and nurturing action are combined with an unchanged perspiration.

Foam formulations known so far mostly contain conventional surfactants/emulsifiers that serve for the stabilization of the emulsion and for the resulting foam stability.

However, as discussed before, conventional emulsifiers or surfactants are repeatedly cited as the cause of incompatibilities of skin care products. Nonetheless, the addition of suitable stabilizers is necessary, because disperse systems, as described above, e.g. emulsions, are thermodynamically instable.

The above described Pickering emulsions are an option to avoid conventional emulsifiers. In EP 1 352 639 A1 and DE 101 62 840, Pickering emulsions are described which are, however, used as emulsions in the form of lotions, creams and gels.

In WO 2004/017930, further Pickering emulsions are described which are characterized especially by a low viscosity and, therefore, are suitable for dermatological cloths. Such thin fluid Pickering emulsions can even be sprayed under formation of a haze.

In WO 2008/138894, foam formulations on the basis of emulsifier-free Pickering emulsions are described.

WO 2008/155389 describes foam formulations on the basis of emulsions the oil phase of which comprises at least one membrane-forming substance forming in the foam formulation lamellar arranged membranes, wherein the emulsions are preferably emulsifier-free.

However, none of the above-described documents describes foam formulations on the basis of emulsifier-free emulsions, which are stabilized by ionic, surface active polymers with a molecular weight of more than 5000 g/mol, wherein the ionic polymer is a copolymer comprising as monomer units an ionic monomer (M1) and at least one further monomer.

SUMMARY OF THE INVENTION

The applicant has now found that oil-in-water emulsions comprising at least one surface active, ionic polymer with a molecular weight of more than 5000 g/mol, wherein the ionic polymer is a copolymer, comprising as monomer units an ionic monomer (M1) and at least one further monomer, are suitable as a basis for foam formulations. Thereby, the positive characteristics of foam formulations are combined with those of polymer-stabilized emulsions. In particular, foam formulations without conventional emulsifiers or with very low contents of conventional emulsifiers can be produced that combine the positive characteristics of the foam, namely the physical structure and the pleasant applicability, with the positive characteristics of polymer-stabilized emulsions, such as their good skin compatibility. This makes such foam formulations especially useful for cosmetic and dermatological formulations for sensitive skin types. Compatibility and user friendliness are advantageously combined.

It is not self-evident that the foaming of oil-in-water emulsions comprising at least one surface active, ionic polymer with a molecular weight of more than 5000 g/mol, wherein the ionic polymer is a copolymer, comprising as monomer units an ionic monomer (M1) and at least one further monomer, results in stable foam products. Foams are obtained, as already mentioned, e.g. by incorporating (pressure) liquefied propellants into O/W-emulsion systems. When the propellant dissolved in the dispersed oil phase evaporates upon foaming, a foam (gas-in-liquid dispersion) is formed. The evaporation and expansion of the propellant dissolved in the dispersed oil phase leads to a dilatation of the dispersed oil phase. It has now been surprisingly found that the polymer gel structure formed at the phase interface is able to withstand the dilatation stress and that upon foaming of the foam formulations according to the invention, no breaking of the formulation occurs and a foam is formed that is suitable for use in pharmaceutical and cosmetic products. The latter is stable enough in order to be, e.g. applied to the skin.

In particular, it has been surprisingly found that an oil-in-water emulsion comprising at least one surface active, ionic polymer with a molecular weight of more than 5000 g/mol, wherein the ionic polymer is a copolymer, comprising as monomer units an ionic monomer (M1) and at least one further monomer, as well as at least one solid emulsifier, is a particularly suitable basis for foam formulations. Foam formulations made thereof exhibit in particular an improved stability in comparison to the foam formulations known in the art which are made from Pickering emulsions, as well as to the above-mentioned, solely polymer-stabilized foam formulations.

Thus, the invention relates to foam formulations comprising a substantially emulsifier-free emulsion of the oil-in-water type, comprising an oil phase and an aqueous phase, the emulsion comprising at least one surface active, ionic polymer with a molecular weight of more than 5000 g/mol, wherein the ionic polymer is a copolymer, comprising as monomer units an ionic monomer (M1) and at least one further monomer. Preferably, the foam formulations according to the invention further contain at least one solid emulsifier.

Furthermore, the invention relates to the use of a substantially emulsifier-free emulsion of the oil-in-water type, comprising an oil phase and an aqueous phase, the emulsion comprising at least one surface active, ionic polymer with a molecular weight of more than 5000 g/mol, wherein the ionic polymer is a copolymer, comprising as monomer units an ionic monomer (M1) and at least one further monomer, for the manufacture of a foam formulation.

Furthermore, the invention relates to the use of at least one surface active, ionic polymer with a molecular weight of more than 5000 g/mol, wherein the ionic polymer is a copolymer, comprising as monomer units an ionic monomer (M1) and at least one further monomer, for the stabilization of foam formulations comprising a substantially emulsifier-free emulsion of the oil-in-water type.

Furthermore, the invention relates to the use of the foam formulations according to the invention as a carrier for active agents, as skin care agent, as skin cleaning agent or as sunscreen. Therefore, the foam formulation can be used for the manufacture of a cosmetic, a medical product or a pharmaceutical composition.

Moreover, the invention comprises a method for the manufacture of foam formulations according to the invention. The method comprises the steps of:
a) preparing an emulsion of the oil-in-water type
b) filling the emulsion with a propellant into a pressurized container, or
c) filling the emulsion into a container other than a pressurized container that upon dispensing of the emulsion generates a foam.

DETAILED DESCRIPTION OF THE INVENTION

1. Definitions

Figure 1:
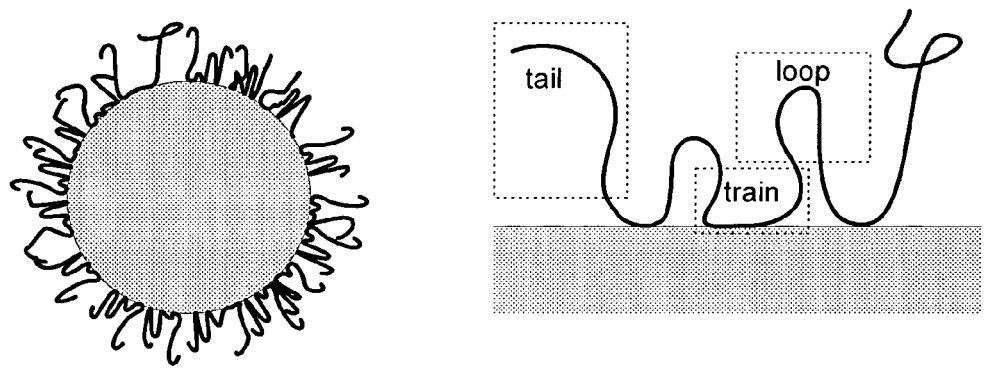
FIG. 1 depicts the schematic structure of a macromolecular interfacial film according to the tail-loop-train-model.
Figure 2:
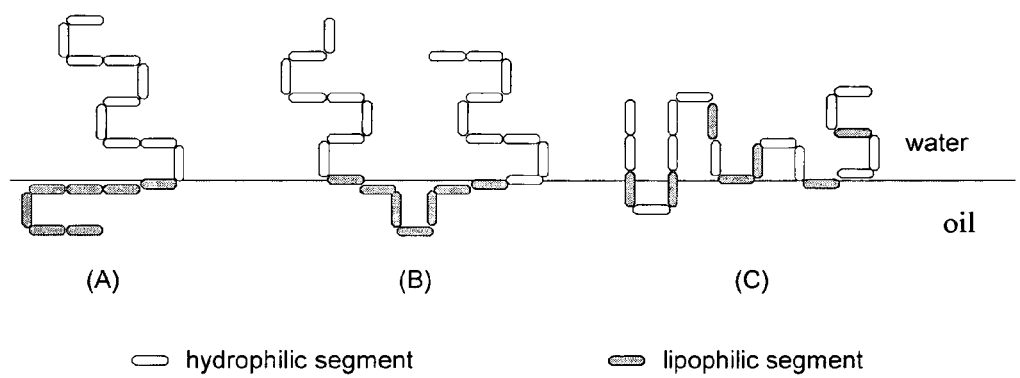
FIG. 2 depicts schematically the possible arrangements of a copolymeric emulsifier, depending on the distribution of the lipophilic and hydrophilic segments in case of A-B-block copolymers (A), A-B-A-block copolymers (B) and copolymers having a random distribution of hydrophilic segments and segments with lower polarity (C).

According to the present invention, foam formulations are formulations, in particular emulsions, that are evidently adapted for the formation of a foam. In particular, the formulations may be filled, either together with a (pressure) liquefied propellant into a pressurized container, or without propellant into a container other than a pressurized container that allows for the formation of a foam upon dispensing of the formulation/emulsion. For example, pump spray containers may be used.

According to the present invention, substantially emulsifier-free emulsions are emulsions that contain less than 0.5 weight-%, preferably less than 0.3 weight-%, more preferably less than 0.1 weight-% and particularly preferred less than 0.05 weight-% of conventional emulsifiers. According to the invention, emulsifier-free emulsions are emulsions that do not contain any conventional emulsifiers.

According to an aspect, conventional emulsifiers according to the present invention are anionic, cationic, amphoteric and non-ionic surfactants. Typical representatives of anionic surfactants are neutralized branched and/or unbranched, saturated or unsaturated fatty acids having a chain length of 10 to 40 carbon atoms. Typical representatives of cationic surfactants are ammonium compounds. Typical representatives of non-ionic surfactants have a hydrophilic part of the molecule, such as glycerol, polyglycerol, sorbitan, carbohydrates or polyoxyethylene glycols, that is connected by means of ester and/or ether bonds to the lipophilic part of the molecule which typically consists of fatty alcohols, fatty acids or iso-fatty acids. For example, polyethoxylated fatty acid esters having a chain length of 10 to 40 carbon atoms and a degree of ethoxylation of 5 to 100 belong to this group. Furthermore, saturated and/or unsaturated, branched and/or unbranched fatty alcohols having a chain length of 10 to 40 carbon atoms belong to the group of non-ionic emulsifiers. Conventional emulsifiers are often used in combinations. Conventional emulsifiers in the sense of the present description are specified in the publications: Pflegekosmetik, 4th edition, Wissenschaftliche Verlagsgesellschaft mbH Stuttgart, pages 151 to 159 and Fiedler Lexikon der Hilfsstoffe, 5th edition, Editio Cantor Verlag Aulendorf, pages 97 to 121.

According to a further aspect of the invention, conventional emulsifiers according to the present invention are all amphiphilic substances with a molecular weight of <5000 g/mol that, in higher concentration, may form micelles and/or other liquid crystalline aggregates.

According to an even further aspect, conventional emulsifiers are all surface active substances that are present in the emulsion neither as solid nor as polymer, especially under conventional storage and application temperatures, such as e.g. room temperature. This means that e.g. the above-described fatty alcohols with a chain length of 10 to 40 carbon atoms fulfill the definition of a conventional emulsifier, as far as they are present in an emulsion, due to the formulation/composition thereof, not as a solid, but e.g. in liquid crystalline or dissolved form. In contrast, if the fatty alcohols with a chain length of 10 to 40 carbon atoms are present in the emulsion as a solid, they do not fulfill the definition of a conventional emulsifier.

According to the invention, a solid emulsifier is a particulate substance that is wettable by both lipophilic and hydrophilic liquids. Solid emulsifiers may be inorganic or organic solids. Furthermore, the particles may be untreated or coated. The particle size is preferably between 1 nm and 200 nm, more preferably between 5 nm and 100 nm. In case of organic solid emulsifiers such as crystalline fatty acids, crystalline fatty acid esters or crystalline fatty alcohols, the particle size is preferably between 1 nm and 1000 nm.

According to the invention, a free acid or a free acid functional group is a compound with an acid function or an acid function, respectively, which is not neutralized to an extent of at least 98%, preferably at least 99% and particularly preferred of 100%.

According to the invention, a completely neutralized acid or a completely neutralized acid functional group is a compound with an acid function or an acid function, respectively, that is neutralized and present in the form of its salts to an extent of at least 98%, preferably at least 99% and particularly preferred of 100%.

According to the invention, a partially neutralized acid or a partially neutralized acid functional group is a compound with an acid function or an acid function, respectively, that is neutralized and present in the form of its salts to an extent of at least 2%, preferably at least 1%, and of at most 98%, preferably of at most 99%, while the non-neutralized fraction is present as a free acid.

According to the invention, "stabilization of a foam formulation" means that, due to the presence of an emulsifier polymer, in particular of a combination of the emulsifier polymer and a solid emulsifier, the structure of the foam formed from the foam formulation can be maintained for a longer period of time before the foam collapses, e.g. for a duration of at least 30 seconds, preferably at least 1 minute and particularly preferred of at least 2 minutes.

According to the invention, the expression "cyclic and linear N-vinyl carboxylic acid amides having a carbon chain of 2 to 9 carbon atoms" relates (i) in the case of cyclic amides to the number of carbon atoms in the cycle (e.g. in the case of N-vinylpyrrolidone the number of carbon atoms is 4), and (ii) in the case of linear amides to the chain length of the carboxylic acid moiety (e.g. in the case of N-vinyl acetamide, the respective number is 2).

2. Composition of the Foam Formulations According to the Present Invention

The foam formulations according to the present invention are based on a substantially emulsifier-free emulsion of the oil-in-water type, comprising an oil phase and an aqueous phase, wherein the emulsion comprises at least one surface active, ionic polymer with a molecular weight of more than 5000 g/mol.

The at least one surface active, ionic polymer with a molecular weight of more than 5000 g/mol is a copolymer comprising as monomer units an ionic monomer (M1) and at least one further monomer. In the following, such polymers are also referred to as emulsifier-copolymers.

Preferably, the oil-in-water emulsion further comprises at least one solid emulsifier.

In a preferred embodiment, the emulsion does not comprise any conventional emulsifiers.

In a further embodiment the foam formulations according to the present invention comprise an emulsion of the oil-in-water type, comprising an oil phase and an aqueous phase, wherein the emulsion comprises an emulsifier system, the emulsifier system consisting substantially of:

a) at least one solid emulsifier, and
b) at least one surface active, ionic polymer with a molecular weight of more than 5000 g/mol, wherein the ionic polymer is a copolymer, comprising as monomer units an ionic monomer (M1), and at least one further monomer.

The expression "emulsifier system consisting substantially of" means that the emulsifier system may contain, if applicable, small amounts of conventional emulsifiers. However, the amount of conventional emulsifiers must then be low enough that the emulsion comprising the emulsifier system is a "substantially emulsifier-free emulsion" according to the present invention. In a preferred embodiment, the emulsifier system consists of the at least one solid emulsifier and the at least one emulsifier-(co)polymer. Apart from the emulsifiers of the emulsifier system, the oil-in-water emulsion on which the foam formulation is based does not comprise any further emulsifiers.

Alternatively or additionally, the at least one surface active, ionic polymer with a molecular weight of more than 5000 g/mol may be described as a polymer that stabilizes the emulsion by the formation of a gel structure at the oil/water phase interface. Such emulsifier polymers may be anionic, cationic or zwitterionic.

Preferably, the gel structure formed at the oil/water phase interface is present in the form of a layer of gel droplets surrounding the oil phase, wherein the gel droplets are preferably strongly hydrated. The presence of such gel structures can be proved by interfacial-rheology measurements.

In a further embodiment, the surface active, ionic polymer which stabilizes the emulsion by the formation of a gel structure at the oil/water phase interface, additionally acts as thickener, i.e. besides the formation of a gel structure at the oil/water phase interface, the viscosity of the surrounding aqueous phase is also increased. The gel structure at the oil/water phase interface preferably has a higher viscosity than the aqueous phase surrounding the gel structure.

Preferably, the at least one surface active, ionic polymer with a molecular weight of more than 5000 g/mol, which stabilizes the emulsion by formation of a gel structure at the oil/water phase interface, is a copolymer comprising as monomer units an ionic monomer (M1) and at least one further monomer (i.e. is an emulsifier-copolymer).

The at least one surface active, ionic polymer with a molecular weight of more than 5000 g/mol is preferably water-soluble or water swellable, particularly preferred water swellable. In the context of the present invention, "water swellable" means that upon contact with water, the polymer hydrates accompanied by a volume increase.

Preferably, the emulsion contains the at least one surface active, ionic polymer with a molecular weight of more than 5000 g/mol in an amount of approximately 0.01 to approximately 10 weight-%, preferably of approximately 0.05 to approximately 8 weight-%, more preferably of approximately 0.1 to approximately 5 weight-%, particularly preferred of approximately 0.2 to approximately 2 weight-%, and most preferred of approximately 0.2 to approximately 1 weight-%, based on the total weight of the emulsion (without propellant).

Emulsifier-Copolymers:

As discussed herein before, the emulsifier-copolymers used according to the present invention contain as monomer units an ionic monomer (M1) and at least one further monomer. The at least one further monomer is different from the ionic monomer (M1).

An emulsifier-copolymer which contains one further monomer is a bipolymer, in the case of two further monomers it is a terpolymer, etc. According to the present invention, bipolymers, terpolymers, quaterpolymers, etc. are all comprised by the term copolymer.

In the context of the present invention, copolymers containing intramolecular cross-linkages are referred to as cross-linked copolymers or cross-polymers.

Preferably, the at least one further monomer has a different polarity than the ionic monomer (M1). The term "polarity" shall be understood according to its usual meaning in the technical field. Polarity refers to a bond of separated charges, caused by a shift of charges in atomic groups, resulting in the atomic group being no longer electrically neutral. The electric dipole moment is a measure for the polarity of a molecule. Depending on the value of the overall dipole moment of a molecule, which is the result of a vectorial addition of the individual dipole moments, a substance is more or less polar, with a smooth transition from extremely polar to completely non-polar. For example, the further monomer has a different polarity than the ionic monomer (M1) if it is a non-ionic monomer which has, by definition, a lower polarity than an ionic compound. However, the further monomer of different polarity may also be an ionic monomer. If the latter contains besides its ionic functionality, e.g. a long, hydrophobic fatty acid chain, it may overall have a smaller polarity than an ionic monomer (M1), which does not contain a hydrophobic part.

The at least one further monomer is preferably selected from the group consisting of ionic monomers, non-ionic monomers and mixtures thereof. Particularly preferred, the at least one further monomer comprises at least one non-ionic monomer.

Ionic Monomer (M1):

The ionic monomer (M1) is preferably anionic, cationic or zwitterionic, particularly preferred anionic.

Preferably, the ionic monomer (M1) contains free, partially neutralized or completely neutralized acid functional groups. A monomer containing free acid functional groups is to be understood as ionic monomer because the acid functional groups may be at least partially neutralized either during the manufacture of the copolymer or during the manufacture of the oil-in-water emulsion.

The acid functional groups are preferably selected from the group consisting of sulfonic acid groups, carboxylic acid groups, phosphoric acid groups, phosphonic acid groups and mixtures thereof.

In a preferred embodiment, the ionic monomer (M1) is selected from the group consisting of acrylic acids, methacrylic acids, crotonic acids, maleic acids, fumaric acids, styrene sulfonic acids, vinyl sulfonic acids, vinyl phosphonic acids, allyl sulfonic acids, methallyl sulfonic acids, acrylamido alkylsulfonic acids, which may each be present as free acid, partially or completely neutralized in the form of their salts, preferably the alkali metal salts, alkaline-earth metal salts, ammonium salts or alkanol ammonium salts; or as anhydride, and mixtures thereof. In a particular preferred embodiment, the ionic monomer (M1) is selected from the group consisting of acrylic acids, methacrylic acids, and acrylamido alkylsulfonic acids.

The ionic monomer (M1) is preferably an acrylamido alkylsulfonic acid, such as 2-acrylamido-2-methylpropane sulfonic acid. Particularly preferred, the acrylamido alkylsulfonic acid is present partially or completely neutralized as alkali metal salt, alkaline-earth metal salt, ammonium salt or alkanol ammonium salt, particularly preferred as sodium or ammonium salt, most preferred as ammonium salt.

Particularly preferred, the acrylamido alkylsulfonic acid has the general formula (1),

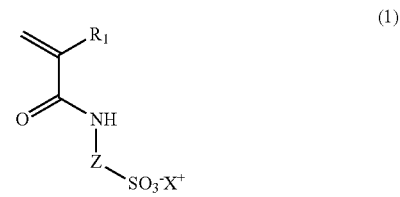

(1)

wherein $R_1$ is selected from the group consisting of hydrogen, methyl or ethyl, Z is a $(C_1-C_8)$-alkylene, that may be unsubstituted or substituted with one or more $(C_1-C_4)$-alkyl groups, and $X^+$ is selected from the group consisting of $H^+$, an alkali metal ion, an alkaline-earth metal ion, an ammonium ion, an alkanol ammonium ion, or mixtures thereof. Preferably, $X^+$ is selected from the group consisting of $H^+$, $Na^+$, $NH_4^+$, or mixtures thereof.

In a particularly preferred embodiment of the invention, the acrylamido alkylsulfonic acid or the ionic monomer (M1) is 2-acrylamido-2-methylpropane sulfonic acid (AMPS, 2-methyl-2-[(1-oxo-2-propenyl)amino]-1-propanesulfonic acid), having the chemical formula (2),

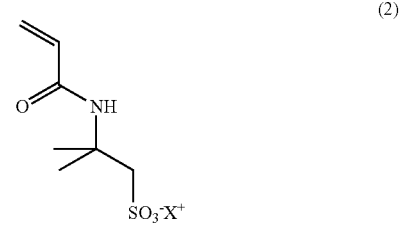

(2)

and may be present as free acid ($X^+$ is $H^+$), or partially or completely neutralized in the form of its salts (the acryloyldimethyltaurates, $X^+$ is a cation except $H^+$, e.g. an alkali metal ion such as $Na^+$, an alkaline-earth metal ion such as (½) $Ca^{2+}$, or an ammonium ion, such as $NH_4^+$). Preferably, $X^+$ is selected from the group consisting of $H^+$, $Na^+$, $NH_4^+$, or mixtures thereof. Particularly preferred, the ionic monomer (M1) is sodium acryloyldimethyltaurate or ammonium acryloyldimethyltaurate ($X^+$ is $Na^+$ and $NH_4^+$, respectively).

In alternative embodiments, the ionic monomer (M1) is an acrylic acid and/or a methacrylic acid.

Further Monomer:

In one embodiment, the at least one further monomer comprises at least one non-ionic monomer, preferably selected from the group consisting of styrenes, chlorostyrenes, di-($C_1$-$C_{30}$)-alkylamino styrenes, vinyl chlorides, isoprenes, vinyl alcohols, vinyl methyl ethers, ($C_1$-$C_{30}$)-carboxylic acid vinyl esters, preferably vinyl acetates and vinyl propionates; acrylic acid esters, methacrylic acid esters, maleic acid esters, fumaric acid esters, crotonic acid esters; in particular linear and branched ($C_1$-$C_{30}$)-alkyl esters of acrylic acid, methacrylic acid, maleic acid, fumaric acid and crotonic acid; linear and branched ($C_1$-$C_{30}$)-hydroxyalkyl esters of acrylic acid, methacrylic acid, maleic acid, fumaric acid and crotonic acid; ethoxylated ($C_1$-$C_{30}$)-alkyl esters of acrylic acid, methacrylic acid, maleic acid, fumaric acid and crotonic acid with from 1 to 40 ethylene oxide units; acrylamides, in particular N,N-di-($C_1$-$C_{30}$)-alkyl acrylamides, methacrylamides, in particular N,N-di-($C_1$-$C_{30}$)-alkyl methacrylamides, cyclic and linear N-vinyl carboxylic acid amides with a carbon chain of 2 to 9 carbon atoms, preferably N-vinylpyrrolidone; and mixtures thereof.

The at least one further monomer may also comprise at least one ionic monomer, preferably selected from the group consisting of acrylic acids, methacrylic acids, crotonic acids, maleic acids, fumaric acids, styrene sulfonic acids, vinyl sulfonic acids, vinyl phosphonic acids, allyl sulfonic acids, methallyl sulfonic acids, acrylamido alkylsulfonic acids, which may each be present as free acid, partially or completely neutralized in the form of their salts, preferably the alkali metal salts, alkaline-earth metal salts or ammonium salts; or as anhydride, and mixtures thereof. In a preferred embodiment, the at least one further monomer comprises an acrylic acid, that is present partially or completely neutralized in the form of its alkaline metal salt, alkaline-earth metal salt or ammonium salt. Particularly preferred, the at least one further monomer comprises sodium acrylate.

A particularly suitable emulsifier-copolymer is for example sodium acrylate/sodium acryloyldimethyltaurate copolymer, in particular in the form of the product available from the company Seppic under the designation 8885MP2 (Sepinov EG-P). Another particularly suitable emulsifier-copolymer is sodium acrylate/acryloyldimethyltaurate/dimethylacrylamide crosspolymer, in particular in the form of the product available from the company Seppic under the designation 8732MP (Sepinov P88). A further particularly suitable emulsifier-copolymer is hydroxyethyl acrylate/sodium acryloyldimethyltaurate copolymer, particularly in the form of the product marketed by the company Seppic under the trade name Sepinov™ EMT 10.

A particularly suitable emulsifier-copolymer is acryloyldimethyltaurate/vinylpyrrolidone copolymer, preferably ammonium acryloyldimethyltaurate/vinylpyrrolidone copolymer, in particular in the form of the product marketed under the trade name Aristoflex® AVC.

Acryloyldimethyltaurate/vinylpyrrolidone copolymer has preferably the general formula (3)

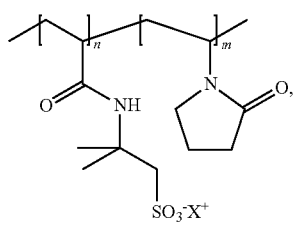

(3)

wherein $X^+$ is $Na^+$ or $NH_4^+$, and n and m are integers that vary independently from each other between 1 to 10,000. In this respect, the polymer is preferably a statistical copolymer, a block copolymer or a graft copolymer, particularly preferred a statistical copolymer.

In alternative preferred embodiments, wherein the ionic monomer (M1) is an acrylic acid and/or a methacrylic acid, the at least one further monomer is preferably selected from the group consisting of cyclic and linear N-vinyl carboxylic acid amides having a carbon chain of 2 to 9 carbon atoms, linear and branched ($C_1$-$C_{30}$)-alkyl esters of acrylic acid, linear and branched ($C_1$-$C_{30}$)-alkyl esters of methacrylic acid, linear and branched ($C_1$-$C_{30}$)-hydroxyalkyl esters of acrylic acid, linear and branched ($C_1$-$C_{30}$)-hydroxyalkyl esters of methacrylic acid, and mixtures thereof. In particular, the at least one further monomer may be selected from the group consisting of cyclic and linear N-vinyl carboxylic acid amides having a carbon chain of 2 to 9 carbon atoms, linear and branched ($C_1$-$C_6$)-alkyl esters of acrylic acid, linear and branched ($C_1$-$C_6$)-alkyl esters of methacrylic acid, and mixtures thereof.

In a preferred embodiment, the ionic monomer (M1) is acrylic acid, and the at least one further monomer is a cyclic or linear N-vinyl carboxylic acid amide having a carbon chain of 2 to 9 carbon atoms.

Such copolymers, their preparation and use in hairstyling products are described e.g. in WO 2006/044193 A2.

The cyclic or linear N-vinyl carboxylic acid amides mentioned above are preferably selected from the group consisting of N-vinyl pyrrolidone, N-vinyl caprolactame, N-vinyl acetamide, or N-vinyl-N-methylacetamide. Preferably the N-vinyl carboxylic acid amide having a carbon chain of 2 to 9 carbon atoms is N-vinyl pyrrolidone.

A particularly suitable emulsifier-copolymer in this regard is for example acrylic acid/N-vinyl pyrrolidone copolymer, in particular in the form of the product UltraThix P-100 (INCI-name: acrylic acid/VP Crosspolymer). UltraThix P-100 which is a lightly crosslinked copolymer of vinyl pyrrolidone and acrylic acid is marketed by the company ISP.

The weight ratio of acrylic acid to N-vinyl pyrrolidone in the acrylic acid/N-vinyl pyrrolidone copolymer may preferably be in the range of 1:3 to 3:1, more preferably of 1:2 to 2:1, most preferably is equal to 1:1.

In a further preferred embodiment, the ionic monomer (M1) is methacrylic acid and the at least one further monomer is selected from one or more, linear or branched ($C_1$-$C_6$)-alkyl esters of acrylic acid or methacrylic acid, preferably from one or more linear or branched ($C_1$-$C_6$)-alkyl esters of acrylic acid, more preferably from one or more of methyl acrylate, ethyl acrylate, n-propyl acrylate, i-propyl acrylate, n-butyl acrylate, i-butyl acrylate, tert-butyl acrylate, and mixtures thereof.

A particularly suitable emulsifier-copolymer in this regard is for example a terpolymer of tert-butyl acrylate, ethyl acrylate and methacrylic acid, in particular in the form of the product Luvimer® 100 P (INCI-name: Acrylates copolymer). Polymers of the Luvimer® series (such Luvimer® 100 P, Luvimer® 36 D and Luvimer® 30 E) are marketed by the company BASF AG.

The applicant has furthermore surprisingly found that particularly stable and fine-pored foams can be obtained when the foam formulations according to the present invention contain a combination of a) a copolymer of acrylic acid and a cyclic or linear N-vinyl carboxylic acid amide having a carbon chain of 2 to 9 carbon atoms, such as acrylic acid/N-vinyl pyrrolidone copolymer and
b) a copolymer of methacrylic acid and one or more linear or branched ($C_1$-$C_6$)-alkyl esters of acrylic acid, such as tert-butyl acrylate/ethyl acrylate/methacrylic acid terpolymer.

Hence in preferred embodiments of the present invention the at least one surface active, ionic polymer comprises acrylic acid/N-vinyl pyrrolidone copolymer and/or tert-butyl acrylate/ethyl acrylate/methacrylic acid terpolymer.

According to a further aspect of the present invention the at least one surface active, ionic polymer is preferably selected from the group consisting of acryloyldimethyltaurate/vinylpyrrolidone copolymer, sodium acrylate/acryloyldimethyltaurate/dimethylacrylamide crosspolymer, hydroxyethyl acrylate/sodium acryloyldimethyltaurate copolymer, sodium acrylate/sodium acryloyldimethyltaurate copolymer, acrylic acid/N-vinyl pyrrolidone copolymer, tert-butyl acrylate/ethyl acrylate/methacrylic acid terpolymer, and mixtures thereof.

Preferably, the emulsifier-copolymers are used in pre-neutralized form, wherein they are preferably in powder form. Alternatively, the emulsifier-copolymers may at least be partially neutralized during the production of the emulsion, e.g. by adjusting the pH of an aqueous phase containing the emulsifier-copolymer.

In particular embodiments of the present invention, the weight ratio between the ionic monomer (M1) and the at least one further monomer is from 99:1 to 1:99, preferably from 95:5 to 5:95, particularly preferred from 90:10 to 10:90.

The emulsifier-copolymer may be for example a statistical copolymer, a block copolymer or a graft copolymer or mixtures thereof, wherein statistical copolymers are preferred.

In specific embodiments of the present invention, the emulsifier-copolymer is cross-linked, wherein the crossed-linked emulsifier-copolymer contains preferably from 0.001 to 10 weight-%, particularly preferred 0.01 to 10 weight-% of crosslinking agent.

As crosslinking agents may be used for example diallyloxyacetic acid or its salts, trimethylolpropanetriacrylate, trimethylolpropane diallyl ether, ethylene glycol dimethacrylate, diethylene glycol diacrylate, tetraethylene glycol diacrylate, methylene bis(acrylamide), divinylbenzene, diallyl urea, triallylamine, 1,1,2,2-tetraallyloxyethane, acrylic acid allyl ester, methacrylic acid allyl ester, dipropyleneglycol diallyl ether, polyglycol diallyl ether, triethyleneglycol divinylether, or hydrochinone diallyl ether. Other suitable crosslinking agents comprise pentaerythritol triallylether, pentaerythritol triacrylate, or pentaerythritol tetraacrylate.

In a particularly preferred embodiment of the present invention, the at least one surface active, ionic polymer comprises a linear acrylic acid/N-vinyl pyrrolidone copolymer, which is crosslinked with 0.5 to 1.5 weight-%, preferably with about 1 weight-% of pentaerythritol triallylether.

Solid Emulsifiers:

In a preferred embodiment, the emulsion contains at least one solid emulsifier, preferably in an amount of more than 0.5 weight-%, particularly preferred more than 1 weight-%. In particular, the emulsion contains from 0.5 to 7 weight-%, preferably from 0.5 to 5 weight-%, particularly preferred from 0.5 to 3 weight-% of the at least one solid emulsifier. The weight percentages are each based on the total weight of the emulsion without propellant.

If the emulsion contains at least one solid emulsifier, the weight ratio of the at least one solid emulsifier to the at least one ionic, surface active polymer in the emulsion is preferably from 0.5:1 to 10:1, more preferably from 1:1 to 8:1, and particularly preferred from 2:1 to 8:1.

Suitable solid emulsifiers are particulate inorganic or organic solids that are wettable by both lipophilic and hydrophilic liquids. Suitable representatives are e.g. titanium dioxide, in particular coated titanium dioxide (e.g. obtainable from Merck KGaA under the designation Eusolex® T-2000), zinc oxide (e.g. obtainable from BASF AG under the designation Z-Cote Max), silicon dioxide, in particular highly dispersed silicon dioxide, $Fe_2O_3$, veegum, bentonite and ethyl cellulose. Furthermore, aluminium oxide, calcium carbonate, coal, magnesium oxide, magnesium trisilicate, crystalline fatty acids, crystalline fatty acid esters, crystalline fatty alcohols, polymer lattices, e.g. polystyrenes or polymethacrylates and polymer-pseudolattices may be used. Mixtures of the above-mentioned solid emulsifiers may also be used. Preferably, the at least one solid emulsifier is selected from the group consisting of crystalline fatty acids, crystalline fatty acid alkyl esters, crystalline fatty alcohols or mixtures thereof.

For example, the at least one solid emulsifier comprises a crystalline fatty acid, preferably with a chain length of 10 to 40 carbon atoms. The crystalline fatty acid is in particular a saturated fatty acid, preferably selected from the group consisting of myristic acid, palmitic acid, margaric acid, stearic acid and arachidic acid or mixtures thereof.

In a particularly preferred embodiment, the at least one solid emulsifier comprises stearic acid. Stearic acid is available for example from the company Cognis under the name Cutina FS 45.

Furthermore, the at least one solid emulsifier may comprise a crystalline fatty alcohol, preferably with a chain length of 10 to 40 carbon atoms. The crystalline fatty alcohol is in particular a saturated fatty alcohol, preferably selected from the group consisting of myristyl alcohol, cetyl alcohol, heptadecanol, stearyl alcohol, cetylstearyl alcohol, eicosanol or mixtures thereof.

In a particularly preferred embodiment, the at least one solid emulsifier comprises cetylstearyl alcohol. The cetylstearyl alcohol is available for example from the company Cognis under the name Lanette O.

Furthermore, the at least one solid emulsifier may comprise a crystalline fatty acid alkyl ester, preferably cetyl palmitate. Cetyl palmitate is available for example from the company Cognis under the name Cutina CP.

Oil Phase:

Suitable components that may form the oil phase may be selected from polar and non-polar oils or mixtures thereof.

The oil phase of the inventive formulations is advantageously selected from the group of phospholipids, such as lecithin and fatty acid triglycerides, from the group of propylene glycol fatty acid esters or butylene glycol fatty acid esters, from the group of natural waxes of animal or plant origin, from the group of ester oils, from the group of dialkyl ethers and dialkyl carbonates, from the group of branched and unbranched hydrocarbons and waxes as well as from the group of cyclic and linear silicon oils.

In one embodiment the oil phase comprises at least one fatty acid alkyl ester such as oleic acid decyl ester (decyl oleate) or cetearyl isononanoate, and/or at least one fatty alcohol such as 2-octyldodecanol. Furthermore, the oil phase may contain saturated aliphatic hydrocarbons such as paraffin.

Decyl oleate is obtainable for example from the company Cognis under the designation Cetiol V. Cetearyl isononanoate is obtainable for example from the company Cognis under the designation Cetiol SN. 2-Octyldodecanol is obtainable for example from the company Cognis under the designation Eutanol G.

In a preferred embodiment, the oil phase comprises at least one triglyceride.

Preferably, the at least one triglyceride comprises caprylic acid/capric acid triglyceride obtainable under the designation Miglyol 812 of the company Sasol, and mixtures thereof with further oil and wax components.

Furthermore, particularly preferred are triglycerides, in particular caprylic acid/capric acid triglyceride obtainable under the designation Miglyol 812 of the company Sasol/Myritol 312 of the company Cognis.

The emulsions according to the invention preferably contain from 5 to 50 weight-% oil phase, particularly preferred 10 to 35 weight-% and especially preferred 12 to 25 weight-% oil phase. These values each refer to the total weight of the emulsion without propellant.

Aqueous Phase:

The aqueous phase may contain cosmetic adjuvants, e.g. lower alcohols (e.g. ethanol, isopropanol), lower diols or polyols as well as ethers thereof (e.g. propylene glycol, glycerol, butylene glycol, hexylene glycol and ethylene glycol), foam stabilizers and thickeners.

Suitable thickeners are polymeric thickeners that are partially water soluble or at least water dispersible and that form in aqueous systems gels or viscous solutions. They increase the viscosity of the water either by binding water molecules (hydration) or, by incorporating and encapsulating the water into the interwoven macromolecules wherein the movability of the water is decreased. Suitable polymers are:

Modified natural materials, such as cellulose ethers (e.g. hydroxypropyl cellulose ether, hydroxyethyl cellulose and hydroxypropyl methyl cellulose ether);

Natural compounds, such as e.g. xanthan, agar-agar, carrageen, polyoses, starch, dextrines, gelatine, casein;

Synthetic compounds, such as e.g. vinyl polymers, polyethers, polyimines, polyamides and derivates of polyacrylic acid; and Inorganic compounds, such as e.g. polysilicic acid and clay minerals.

Preferably, the emulsion contains at least one thickener selected from the group consisting of hydroxypropyl methyl cellulose, xanthan gum, sodium polyacrylate and mixtures thereof.

A preferred hydroxypropyl methyl cellulose according to the invention is Metolose 90SH 100. The general pharmacopoeial term for hydroxypropyl methyl cellulose is hypromellose.

Xanthan gum is available for example from the company Kelco under the designation Keltrol® CG. Sodium polyacrylate is available for example from the company Cognis under the designation Cosmedia SP.

The emulsions according to the invention preferably contain from 0.2 to 1.5 weight-% of thickener (based on the dry weight of the thickener and the total weight of the emulsion without propellant). Particularly preferred are 0.2 to 0.8 weight-% of thickener. In a further preferred embodiment, the emulsions according to the present invention do not contain polyacrylate (homopolymer) as thickener.

Active Agents:

The optionally contained active agent may be selected from all active agents that can be applied to the surface of the skin, and mixtures thereof. The active agent may act cosmetically or pharmaceutically. Accordingly, cosmetic or dermatological (to be employed as medical product or pharmaceutical composition) foam formulations are obtained. Furthermore, the formulation may be used for protecting the skin against environmental influences. The active agent can be of natural or synthetic origin. The group of active agents may also overlap with other groups of ingredients, such as e.g. the oil component, the thickening agents or the solid emulsifiers. For example, some oil components may also act as active agents, such as e.g. oils having polyunsaturated fatty acids, or solid emulsifiers, such as e.g. particulate titanium dioxide may serve as UV-filter. Depending on their properties, the substances can be assigned to several groups.

Active agents of the inventive formulations are advantageously selected from the group of substances having moisturizing and barrier-strengthening properties, such as e.g. Hydroviton, an emulation of NMF, pyrrolidone carboxylic acid and salts thereof, lactic acid and salts thereof, glycerol, sorbitol, propylene glycol and urea, substances from the group of proteins and protein hydrolysates, such as e.g. collagen, elastin as well as silk protein, substances of the group of glucosaminoglucanes, such as e.g. hyaluronic acid, of the group of carbohydrates, such as e.g. Pentavitin that corresponds in respect of its composition to the carbohydrate mixture of the human corneal layer, and the group of lipids and lipid precursors such as for example ceramides. Further advantageous active agents in the sense of the present invention may further be selected from the group of vitamins, such as e.g. panthenol, niacin, $\alpha$-tocopherol and its esters, vitamin A as well as vitamin C. Moreover, active agents selected from the group of antioxidants e.g. galates and polyphenols may be used. Urea, hyaluronic acid and Pentavitin are preferred substances.

It is further preferred that substances having skin soothing and regenerative action are employed as active agents, such as e.g. panthenol, bisabolol and phytosterols.

In a preferred embodiment, the foam formulation according to the invention contains urea. In a further preferred embodiment, the foam formulation according to the invention contains no $\alpha$- or $\beta$-hydroxycarboxylic acids or salts thereof, in particular no $C_1$-$C_{25}$-$\alpha$- or $C_1$-$C_{25}$-$\beta$-hydroxycarboxylic acids or salts thereof.

Advantageous active agents in the sense of the present invention are also plants and plant extracts. These include e.g. algae, aloe, arnica, barber's rash, comfrey, birch, nettle, calendula, oak, ivy, witch-hazel, henna, hop, camomile, ruscus, peppermint, marigold, rosemary, sage, green tea, tea tree, horsetail, thyme and walnut as well as extracts thereof.

The formulations according to the invention may further contain as active agents antimycotics and antiseptics/disinfectants of synthetic or natural origin.

Further active agents are glucocorticoids, antibiotics, analgetics, antiphlogistics, antirheumatics, antiallergics, antiparasitics, antipruriginostics, antipsoriatics, retinoids, local anaesthetics, therapeutic agents for veins, ceratolytics, hyperaemic substances, coronary therapeutic agents (nitrates/nitro-compounds), antiviral drugs, cytostatics, hormones, agents promoting wound healing, e.g. growth factors, enzyme preparations and insecticides.

Further Components of the Emulsion:

Furthermore, the formulations may optionally contain colouring agents, pearlescent pigments, fragrances/perfum, sunscreen filter substances, preservatives, complex formers, antioxidants and repellent agents as well as pH-regulators. However, in a preferred embodiment, the formulations according to the invention are free of substances that may irritate the skin and are in particular free of fragrances/perfum, colouring agents and conventional emulsifiers.

The foam formulations according to the invention may contain, apart from the components already described above, further natural fats such as e.g. shea butter, neutral oils, olive oil, squalane, ceramides and moisturing substances as usual in the art.

The above list of individual components of the emulsion should be understood in the sense that individual exemplified components due to their diverse properties may also be assignable to several groups.

Propellants:

Suitable propellants are e.g. $N_2O$, propane, butane and i-butane. The complete foam formulation contains for example from 1 to 20 weight-%, from 2 to 18 weight-% or from 5 to 15 weight-%, preferably approximately 10 weight-% of propellant. (Pressure) liquefied propellant is used for charging the emulsion with propellant.

3. Method of Manufacture

The foam formulations according to the invention are prepared by providing an emulsion of the oil-in-water type and filling said emulsion and optionally charging with a propellant into a suitable container, preferably into a pressurized container. As an alternative to a propellant and a pressurized container, the polymer-stabilized emulsion may also be filled into a different container that is suitable to dispense the emulsion as a foam even in the absence of propellant. Such systems are known to the person skilled in the art.

In particular, the method for manufacturing the emulsion comprises the following steps:
 (1) providing a liquid oil phase,
 (2) providing an aqueous phase containing at least one surface active, ionic polymer with a molecular weight of more than 5000 g/mol, wherein the ionic polymer is a copolymer, comprising as monomer units
  an ionic monomer (M1), and
  at least one further monomer,
 (3) mixing and homogenizing the aqueous phase with the oil phase.

In a preferred embodiment, the liquid oil phase of step (1) is provided in the form of a clear melt, preferably by heating to a temperature of from 60 to 90° C., particularly preferred of from 60 to 80° C., most preferred of approximately 70° C., and is optionally subsequently cooled to the temperature used in step (3).

Preferably, the mixing and the homogenizing of the aqueous phase with the oil phase in step (3) is performed at a temperature of from 25 to 60° C., more preferably of from 30 to 50° C., particularly preferred of from 35 to 45° C., and most preferred of approximately 40° C.

If the polymer-stabilized emulsion comprises at least one solid emulsifier, the liquid oil phase provided in step (1) preferably contains at least one solid emulsifier.

If the polymer-stabilized emulsion comprises at least one thickener, the oil phase provided in step (1) preferably contains at least one thickener, and/or the aqueous phase provided in step (2) preferably contains at least one thickener, and/or the method preferably comprises the following further steps:
 (4) providing an aqueous thickener solution,
 (5) mixing of the thickener solution with the emulsion obtained in step (3).

According to a further embodiment of the present invention, the method of manufacturing the polymer-stabilized emulsion comprises the following steps:
 (1) providing a liquid oil phase,
 (2) providing an aqueous phase,
 (3) mixing and homogenizing the aqueous phase with the oil phase to obtain an emulsion,
 (4) providing a further aqueous phase containing at least one surface active, ionic polymer with a molecular weight of more than 5000 g/mol, wherein the ionic polymer is a copolymer, comprising as monomer units
  an ionic monomer (M1), and
  at least one further monomer,
 (5) mixing of the further aqueous phase with the emulsion obtained in step (3).

In a preferred embodiment, the liquid oil phase of step (1) is provided in the form of a clear melt, preferably by heating to a temperature of from 60 to 90° C., particularly preferred of from 60 to 80° C., and most preferred of approximately 70° C., and is optionally subsequently cooled to the temperature used in step (3).

Preferably, the mixing and homogenizing of the aqueous phase with the oil phase in step (3) is performed at a temperature of from 25 to 60° C., more preferably of from 30 to 50° C., particularly preferred of from 35 to 45° C., and most preferred of approximately 40° C.

In a preferred embodiment, the mixing of the further aqueous phase with the emulsion of step (5) is performed at a temperature of from 10 to 30° C., preferably of from 15 to 25° C. and particularly preferred at room temperature.

If the polymer-stabilized emulsion comprises at least one solid emulsifier, the liquid oil phase provided in step (1) preferably contains at least one solid emulsifier.

If the polymer-stabilized emulsion comprises at least one thickener, the oil phase provided in step (1) preferably contains at least one thickener, and/or the aqueous phase provided in step (2) preferably contains at least one thickener, and/or the further aqueous phase provided in step (4) preferably contains at least one thickener, and/or the method preferably comprises the following further steps:
 (6) providing an aqueous thickener solution,
 (7) mixing of the thickener solution with the emulsion obtained in step (5).

If in any of the above described methods, the at least one surface active, ionic polymer is not used in pre-neutralized form or if otherwise necessary, preferably the pH value of the aqueous phase containing the at least one surface active, ionic polymer is suitably adjusted, before the aqueous phase is added to the oil phase or to the obtained emulsion. The pH adjustment ensures that the at least one surface active, ionic polymer is at least partially neutralized. For example the pH value may be adjusted to 6-7. For this purpose, any suitable base may be used, such as sodium hydroxide, triethanolamine, triisopropanolamine, diethylaminopropylamine, 2-amino-2-methylpropan-1-ol, or trometamol (2-amino-2-hydroxymethyl-propane-1,3-diol). Trometamol is particularly preferred.

The person skilled in the art understands that combinations of the above-mentioned methods of manufacturing are also possible for the manufacture of polymer-stabilized emulsions used according to the invention.

For the manufacture of the foam formulation, the emulsions manufactured according to the above-mentioned methods are preferably charged with 1 to 20 weight-%, preferably 2 to 18 weight-%, more preferably 5 to 15 weight-%, and particularly preferred 10 weight-% of propellant, based on the weight of the foam formulation. Preferably, the propellant is a pressure-liquefied propellant.

4. Applications

The foam formulations according to the present invention can be employed for all cosmetic and dermatological purposes (as a medical product or pharmaceutical composition). For example, the foam formulations may be employed as skin care agent or skin cleaning agent. Further, they may be used as carriers for active agents and may be employed in the medical dermatological field. In particular, the formulations may be employed as sunscreen. Many of the solid emulsifiers such as for example titanium dioxide are effective UVA and UVB filters.

5. Preferred Embodiments

The present invention is particularly directed to the following preferred embodiments:

1. Foam formulation comprising a substantially emulsifier-free emulsion of the oil-in-water type, comprising an oil phase and an aqueous phase, the emulsion comprising
    at least one surface active, ionic polymer with a molecular weight of more than 5000 g/mol, which stabilizes the emulsion by formation of a gel structure at the oil/water phase interface.
2. Foam formulation comprising a substantially emulsifier-free emulsion of the oil-in-water type, comprising an oil phase and an aqueous phase, wherein the emulsion comprises:
    a) at least one solid emulsifier, and
    b) at least one surface active, ionic polymer with a molecular weight of more than 5000 g/mol, which stabilizes the emulsion by formation of a gel structure at the oil/water phase interface.
3. Foam formulation comprising an emulsion of the oil-in-water type, comprising an oil phase and an aqueous phase, wherein the emulsion comprises an emulsifier system, the emulsifier system consisting substantially of:
    a) at least one solid emulsifier, and
    b) at least one surface active, ionic polymer with a molecular weight of more than 5000 g/mol, which stabilizes the emulsion by formation of a gel structure at the oil/water phase interface.
4. Foam formulation according to any one of embodiments 1 to 3, wherein the ionic polymer is anionic, cationic or zwitterionic, preferably anionic.
5. Foam formulation according to any one of embodiments 1 to 4, wherein the gel structure at the oil/water phase interface is present in the form of a layer of gel droplets surrounding the oil phase.
6. Foam formulation according to embodiment 5, wherein the gel droplets are strongly hydratized.
7. Foam formulation according to any one of embodiments 1 to 6,
    wherein the at least one surface active, ionic polymer further acts as thickener.
8. Foam formulation according to any one of embodiments 1 to 7, wherein the gel structure at the oil/water phase interface has a higher viscosity than the aqueous phase surrounding the gel structure.
9. Foam formulation according to any one of embodiments 1 to 8, wherein the ionic polymer is a copolymer, comprising as monomer units
    an ionic monomer (M1), and
    at least one further monomer.
10. Foam formulation comprising a substantially emulsifier-free emulsion of the oil-in-water type, comprising an oil phase and an aqueous phase, the emulsion comprising
    at least one surface active ionic polymer with a molecular weight of more than 5000 g/mol, wherein the ionic polymer is a copolymer comprising as monomer units
    an ionic monomer (M1), and
    at least one further monomer.
11. Foam formulation comprising a substantially emulsifier-free emulsion of the oil-in-water type, comprising an oil phase and an aqueous phase, wherein the emulsion comprises:
    a) at least one solid emulsifier, and
    b) at least one surface active, ionic polymer with a molecular weight of more than 5000 g/mol, wherein the ionic polymer is a copolymer comprising as monomer units
    an ionic monomer (M1), and
    at least one further monomer.
12. Foam formulation comprising an emulsion of the oil-in-water type, comprising an oil phase and an aqueous phase, wherein the emulsion comprises an emulsifier system, the emulsifier system consisting substantially of:
    a) at least one solid emulsifier, and
    b) at least one surface active, ionic polymer with a molecular weight of more than 5000 g/mol, wherein the ionic polymer is a copolymer comprising as monomer units
    an ionic monomer (M1), and
    at least one further monomer.
13. Foam formulation according to any one of embodiments 1 to 12, wherein the emulsion contains less than 0.5 weight-%, preferably less than 0.3 weight-%, more preferably less than 0.1 weight-% of conventional emulsifiers.
14. Foam formulation according to any one of embodiments 1 to 13, wherein the emulsion contains no conventional emulsifiers.
15. Foam formulation according to any one of embodiments 1 to 14,
    wherein the at least one surface active, ionic polymer is water soluble or water swellable, preferably water swellable.
16. Foam formulation according to any one of embodiments 1 to 15,
    wherein the emulsion contains from about 0.01 to about 10 weight-%, preferably from about 0.05 to about 8 weight-%, more preferably from about 0.1 to about 5 weight-%, particularly preferred from about 0.2 to about 2 weight-%, and most preferred from about 0.2 to about 1 weight-% of the at least one surface active, ionic polymer, based on the total weight of the emulsion (without propellant).
17. Foam formulation according to any one of embodiments 9 to 16,
    wherein the at least one further monomer has a different polarity than the ionic monomer (M1).
18. Foam formulation according to any one of embodiments 9 to 17,
    wherein the at least one further monomer is selected from the group consisting of ionic monomers, non-ionic monomers and mixtures thereof.

19. Foam formulation according to any one of embodiments 9 to 18,
wherein the at least one further monomer comprises at least one non-ionic monomer.
20. Foam formulation according to any one of embodiments 9 to 19,
wherein the ionic monomer (M1) is anionic, cationic or zwitterionic, preferably anionic.
21. Foam formulation according to any one of embodiments 9 to 20,
wherein the ionic monomer (M1) contains free, partially neutralized or completely neutralized acid functional groups.
22. Foam formulation according to embodiment 21,
wherein the acid functional groups are selected from the group consisting of sulfonic acid groups, carboxylic acid groups, phosphoric acid groups, phosphonic acid groups and mixtures thereof.
23. Foam formulation according to any one of embodiments 9 to 22,
wherein the ionic monomer (M1) is selected from the group consisting of acrylic acids, methacrylic acids, crotonic acids, maleic acids, fumaric acids, styrene sulfonic acids, vinyl sulfonic acids, vinyl phosphonic acids, allyl sulfonic acids, methallyl sulfonic acids, acrylamido alkylsulfonic acids, which may each be present as free acid, partially or completely neutralized in the form of their salts, preferably the alkali metal salts, alkaline-earth metal salts, ammonium salts or alkanol ammonium salts; or as anhydride, and mixtures thereof, and preferably the ionic monomer (M1) is selected from the group consisting of acrylic acids, methacrylic acids, and acrylamido alkylsulfonic acids.
24. Foam formulation according to any one of embodiments 9 to 23,
wherein the ionic monomer (M1) is an acrylamido alkylsulfonic acid which is present as free acid, partially or completely neutralized in the form of its salts.
25. Foam formulation according to embodiment 24,
wherein the acrylamido alkylsulfonic acid is partially or completely neutralized and is present as alkali metal salt, alkaline-earth metal salt, ammonium salt or alkanol ammonium salt, preferably as sodium salt or ammonium salt, particularly preferred as ammonium salt.
26. Foam formulation according to any one of embodiments 24 or 25, wherein the acrylamido alkylsulfonic acid is 2-acrylamido-2-methylpropane sulfonic acid.
27. Foam formulation according to any one of embodiments 9 to 25, wherein the ionic monomer (M1) is an acrylamido alkylsulfonic acid having the general formula (1),

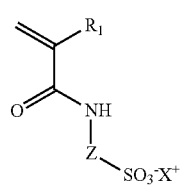
(1)

wherein $R_1$ is selected from the group consisting of hydrogen, methyl or ethyl, Z is a $(C_1$-$C_8)$-alkylene,
that may be unsubstituted or substituted with one or more $(C_1$-$C_4)$-alkyl groups, and $X^+$ is selected from the group consisting of $H^+$, an alkali metal ion, an alkaline-earth metal ion, an ammonium ion, an alkanol ammonium ion, or mixtures thereof, preferably from the group consisting of $H^+$, $Na^+$, $NH_4^+$, or mixtures thereof
28. Foam formulation according to any one of embodiments 9 to 25, wherein the ionic monomer (M1) is 2-acrylamido-2-methylpropane sulfonic acid having the general formula (2)

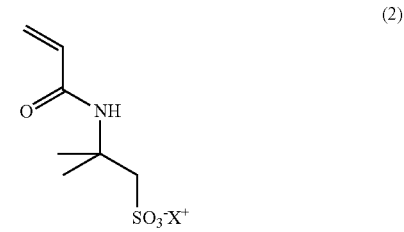
(2)

wherein $X^+$ is selected from the group consisting of $H^+$, an alkali metal ion, an alkaline-earth metal ion, an ammonium ion, an alkanol ammonium ion or mixtures thereof, preferably from the group consisting of $H^+$, $Na^+$, $NH_4^+$ or mixtures thereof.
29. Foam formulation according to any one of embodiments 9 to 28, wherein the ionic monomer (M1) is sodium acryloyldimethyltaurate or ammonium acryloyldimethyltaurate.
30. Foam formulation according to any one of embodiments 9 to 29, wherein the at least one further monomer comprises at least one non-ionic monomer selected from the group consisting of styrenes, chlorostyrenes, di-$(C_1$-$C_{30})$-alkylamino styrenes, vinyl chlorides, isoprenes, vinyl alcohols, vinyl methyl ethers, $(C_1$-$C_{30})$-carboxylic acid vinyl esters, preferably vinyl acetates and vinyl propionates; acrylic acid esters, methacrylic acid esters, maleic acid esters, fumaric acid esters, crotonic acid esters; in particular linear and branched $(C_1$-$C_{30})$-alkyl esters of acrylic acid, methacrylic acid, maleic acid, fumaric acid and crotonic acid; linear and branched $(C_1$-$C_{30}$-hydroxyalkyl esters of acrylic acid, methacrylic acid, maleic acid, fumaric acid and crotonic acid; ethoxylated $(C_1$-$C_{30})$-alkyl esters of acrylic acid, methacrylic acid, maleic acid, fumaric acid and crotonic acid having from 1 to 40 ethylene oxide units; acrylamides, in particular N,N-di-$(C_1$-$C_{30})$-alkyl acrylamides, methacrylamides, in particular N,N-di-$(C_1$-$C_{30})$-alkyl methacrylamides, cyclic and linear N-vinyl carboxylic acid amides having a carbon chain of 2 to 9 carbon atoms, preferably N-vinylpyrrolidone; and mixtures thereof.
31. Foam formulation according to any one of embodiments 9 to 30,
wherein the at least one further monomer comprises at least one non-ionic monomer selected from the group consisting of linear and branched $(C_1$-$C_{30})$-alkyl esters of acrylic acid or methacrylic acid; linear and branched $(C_1$-$C_{30})$-hydroxyalkyl esters of acrylic acid or methacrylic acid; ethoxylated $(C_1$-$C_{30})$-alkyl esters of acrylic acid or methacrylic acid having from 1 to 40 ethylene oxide units; N,N-di-$(C_1$-$C_{30})$-alkyl acrylamides, N,N-di-$(C_1$-$C_{30})$-alkyl methacrylamides, cyclic and linear N-vinyl carboxylic acid amides having a carbon chain of 2 to 9 carbon atoms, preferably N-vinylpyrrolidone; and mixtures thereof 32. Foam formulation according to any one of embodiments 9 to 31,
wherein the at least one further monomer comprises at least one non-ionic monomer selected from the group consisting of linear and branched $(C_1$-$C_6)$-hydroxyalkyl esters of acrylic acid or methacrylic acid, preferably hydroxyethyl acrylate; ethoxylated $(C_1$-$C_{30})$-alkyl esters of acrylic acid or methacrylic acid having from 1 to 40 ethylene oxide units; preferably beheneth-25-methacrylate; N,N-di-$(C_1$-$C_6)$-alkyl acrylamides, preferably N,N-dimethylacrylamides, cyclic and linear N-vinyl carboxylic acid amides having a carbon chain of 2 to 9 carbon atoms, preferably N-vinylpyrrolidone, and mixtures thereof.

33. Foam formulation according to any one of embodiments 9 to 32, wherein the at least one further monomer comprises at least one ionic monomer selected from the group consisting of acrylic acids, methacrylic acids, crotonic acids, maleic acids, fumaric acids, styrene sulfonic acids, vinyl sulfonic acids, vinyl phosphonic acids, allyl sulfonic acids, methallyl sulfonic acids, acrylamido alkylsulfonic acids, which may each be present as free acid, partially or completely neutralized in the form of their salts, preferably the alkali metal salts, alkaline-earth metal salts or ammonium salts; or as anhydride, and mixtures thereof.

34. Foam formulation according to embodiment 33,
wherein the at least one further monomer comprises an acrylic acid which is present partially or completely neutralized in the form of its alkali metal salts, alkaline-earth metal salts or ammonium salts.

35. Foam formulation according to the embodiments 33 or 34,
wherein the at least one further monomer comprises sodium acrylate.

36. Foam formulation according to any one of embodiments 1 to 35,
wherein the at least one surface active, ionic polymer is selected from the group consisting of acryloyldimethyltaurate/vinylpyrrolidone copolymer, sodium acrylate/acryloyldimethyltaurate/dimethylacrylamide crosspolymer, hydroxyethyl acrylate/sodium acryloyldimethyltaurate copolymer, sodium acrylate/sodium acryloyldimethyltaurate copolymer, and mixtures thereof.

37. Foam formulation according to any one of embodiments 1 to 36,
wherein the at least one surface active ionic polymer is acryloyldimethyltaurate/vinylpyrrolidone copolymer, particularly preferred ammonium acryloyldimethyltaurate/vinylpyrrolidone copolymer.

38. Foam formulation according to any one of embodiments 1 to 37,
wherein the at least one surface active, ionic polymer is acryloyldimethyltaurate/vinylpyrrolidone copolymer having the general formula (3),

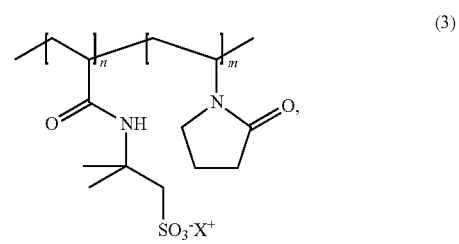

wherein $X^+$ is $Na^+$ or $NH_4^+$, preferably $NH_4^+$, and n and m are integers which vary independently of each other between 1 to 10.000.

39. Foam formulation according to any one of embodiments 1 to 36,
wherein the at least one surface active, ionic polymer is sodium acrylate/acryloyldimethyltaurate/dimethylacrylamide crosspolymer.

40. Foam formulation according to any one of embodiments 1 to 36,
wherein the at least one surface active, ionic polymer is hydroxyethyl acrylate/sodium acryloyldimethyltaurate copolymer.

41. Foam formulation according to any one of embodiments 1 to 36,
wherein the at least one surface active, ionic polymer is sodium acrylate/sodium acryloyldimethyltaurate copolymer.

42. Foam formulation according to any one of embodiments 1 to 23 and 30 to 33, wherein
the ionic monomer (M1) is an acrylic acid and/or a methacrylic acid, and
the at least one further monomer is selected from the group consisting of cyclic and linear N-vinyl carboxylic acid amides having a carbon chain of 2 to 9 carbon atoms, linear and branched $(C_1$-$C_{30})$-alkyl esters of acrylic acid, linear and branched $(C_1$-$C_{30})$-alkyl esters of methacrylic acid, linear and branched $(C_1$-$C_{30})$-hydroxyalkyl esters of acrylic acid, linear and branched $(C_1$-$C_{30})$-hydroxyalkyl esters of methacrylic acid, and mixtures thereof.

43. Foam formulation according to embodiment 42, wherein the at least one further monomer is selected from the group consisting of cyclic and linear N-vinyl carboxylic acid amides having a carbon chain of 2 to 9 carbon atoms, linear and branched $(C_1$-$C_6)$-alkyl esters of acrylic acid, linear and branched $(C_1$-$C_6)$-alkyl esters of methacrylic acid, and mixtures thereof.

44. Foam formulation according to embodiment 42 or 43, wherein the ionic monomer (M1) is acrylic acid and the at least one further monomer is a cyclic or linear N-vinyl carboxylic acid amide having a carbon chain of 2 to 9 carbon atoms.

45. Foam formulation according to any one of embodiments 42 to 44, wherein the cyclic and linear N-vinyl carboxylic acid amide is N-vinyl pyrrolidone, N-vinyl caprolactame, N-vinyl acetamide, or N-vinyl-N-methylacetamide, preferably N-vinyl pyrrolidone.

46. Foam formulation according to embodiments 42 or 43, wherein the ionic monomer (M1) is methacrylic acid and the at least one further monomer is selected from one or more, linear or branched $(C_1$-$C_6)$-alkyl esters of acrylic acid or methacrylic acid, preferably from one or more linear or branched $(C_1$-$C_6)$-alkyl esters of acrylic acid, more preferably from one or more of methyl acrylate, ethyl acrylate, n-propyl acrylate, i-propyl acrylate, n-butyl acrylate, i-butyl acrylate, tert-butyl acrylate, and mixtures thereof.

47. Foam formulation according to any one of embodiments 1 to 23 and 42 to 46, wherein the at least one surface active, ionic polymer comprises a combination of
   a) a copolymer of acrylic acid and a cyclic or linear N-vinyl carboxylic acid amide having a carbon chain of 2 to 9 carbon atoms, and
   b) a copolymer of methacrylic acid and one or more linear or branched ($C_1$-$C_6$)-alkyl esters of acrylic acid.

48. Foam formulation according to any one of embodiments 1 to 23 and 42 to 47, wherein the at least one surface active ionic polymer comprises acrylic acid/N-vinyl pyrrolidone copolymer and/or tert-butyl acrylate/ethyl acrylate/methacrylic acid terpolymer.

49. Foam formulation according to any one of embodiments 1 to 48, wherein the at least one surface active ionic polymer is selected from the group consisting of acryloyldimethyltaurate/vinylpyrrolidone copolymer, sodium acrylate/acryloyldimethyltaurate/dimethylacrylamide crosspolymer, hydroxyethyl acrylate/sodium acryloyldimethyltaurate copolymer, sodium acrylate/sodium acryloyldimethyltaurate copolymer, acrylic acid/N-vinyl pyrrolidone copolymer, tert-butyl acrylate/ethyl acrylate/methacrylic acid terpolymer, and mixtures thereof.

50. Foam formulation according to any one of embodiments 9 to 49,
   wherein the copolymer is used in pre-neutralized form, preferably in pre-neutralized powder form.

51. Foam formulation according to any one of embodiments 9 to 50,
   wherein the weight ratio of the ionic monomer (M1) to the at least one further monomer is from 99:1 to 1:99, preferably from 95:5 to 5:95, particularly preferred from 90:10 to 10:90.

52. Foam formulation according to any one of embodiments 9 to 51,
   wherein the copolymer is cross-linked.

53. Foam formulation according to embodiment 52,
   wherein the copolymer contains from 0.001 to 10 weight-%, preferably from 0.01 to 10 weight-% crosslinking agent.

54. Foam formulation according to embodiment 52 or 53,
   wherein the crosslinking agent is selected from the group consisting of diallyloxyacetic acid or salts thereof, trimethylol propane triacrylate, trimethylol propane diallyl ether, ethylene glycol dimethacrylate, diethylene glycol diacrylate, tetraethylene glycol diacrylate, methylene bis(acrylamide), divinylbenzene, diallyl urea, triallylamine, 1,1,2,2-tetraallyloxyethane, acrylic acid allyl ester, methacrylic acid allyl ester, dipropyleneglycol diallyl ether, polyglycol diallyl ether, triethyleneglycol divinylether, hydrochinone diallyl ether, or mixtures thereof.

55. Foam formulation according to any one of embodiments 9 to 54,
   wherein the copolymer is a statistical copolymer, a block copolymer or a graft copolymer, preferably a statistical copolymer.

56. Foam formulation according to any one of embodiments 2 to 9 and 11 to 55, wherein the emulsion contains more than 0.5 weight-%, preferably more than 1 weight-% of the at least one solid emulsifier, based on the total weight of the emulsion without propellant.

57. Foam formulation according to any one of embodiments 2 to 9 and 11 to 56, wherein the emulsion contains from 0.5 to 7 weight-%, preferably from 0.5 to 5 weight-%, particularly preferred from 0.5 to 3 weight-% of the at least one solid emulsifier, based on the total weight of the emulsion without propellant.

58. Foam formulation according to any one of embodiments 2 to 9 and 11 to 57, wherein the weight ratio of the at least one solid emulsifier to the at least one ionic, surface active polymer in the emulsion is from 0.5:1 to 10:1, preferably from 1:1 to 8:1, most preferably from 2:1 to 8:1.

59. Foam formulation according to any one of embodiments 2 to 9 and 11 to 58, wherein the emulsion comprises at least one particulate solid emulsifier, selected from the group consisting of titanium dioxide, silicon dioxide, $Fe_2O_3$, zinc oxide, veegum, bentonite and ethyl cellulose, aluminium oxide, calcium carbonate, coal, magnesium oxide, magnesium trisilicate, crystalline fatty acids, crystalline fatty acid esters, crystalline fatty alcohols, polymer lattices such as polystyrenes or polymethacrylates, and polymer-pseudolattices or mixtures thereof.

60. Foam formulation according to embodiment 59,
   wherein the emulsion comprises at least one solid emulsifier selected from the group consisting of crystalline fatty acids, crystalline fatty acid alkyl esters, crystalline fatty alcohols or mixtures thereof.

61. Foam formulation according to embodiment 59 or 60,
   wherein the at least one solid emulsifier comprises a crystalline fatty acid, preferably with a chain length of 10 to 40 carbon atoms.

62. Foam formulation according to any one of embodiments 59 to 61,
   wherein the crystalline fatty acid is a saturated fatty acid, preferably selected from the group consisting of myristic acid, palmitic acid, margaric acid, stearic acid and arachidic acid or mixtures thereof, particularly preferred stearic acid.

63. Foam formulation according to any one of embodiments 59 to 62,
   wherein the at least one solid emulsifier comprises a crystalline fatty alcohol, preferably with a chain length of 10 to 40 carbon atoms.

64. Foam formulation according to any one of embodiments 59 to 63,
   wherein the crystalline fatty alcohol is a saturated fatty alcohol, preferably selected from the group consisting of myristic alcohol, cetyl alcohol, heptadecanol, stearyl alcohol, cetylstearyl alcohol, eicosanol, or mixtures thereof, particularly preferred cetylstearyl alcohol.

65. Foam formulation according to any one of embodiments 59 to 64,
   wherein the at least one solid emulsifier comprises a crystalline fatty acid alkyl ester, preferably cetyl palmitate.

66. Foam formulation according to any one of the preceding embodiments, wherein the oil phase comprises at least one triglyceride.

67. Foam formulation according to embodiment 66,
   wherein the triglyceride comprises caprylic acid/capric acid triglyceride.

68. Foam formulation according to any one of the preceding embodiments, wherein the oil phase comprises at least one fatty acid alkyl ester and/or fatty alcohol, preferably selected from the group consisting of decyl oleate, cetearyl isononanoate and 2-octyldodecanol, and mixtures thereof.

69. Foam formulation according to any one of the preceding embodiments, wherein the emulsion comprises at least one thickener.

70. Foam formulation according to any one of the preceding embodiments, wherein the emulsion comprises from 0.2 to 1.5 weight-% thickener, preferably from 0.2 to 0.8 weight-% thickener, based on the dry weight of the thickener and the total weight of the emulsion without propellant.

71. Foam formulation according to embodiment 69 or 70, wherein the thickener is selected from the group consisting of xanthan gum, sodium polyacrylate, hydroxypropyl methyl cellulose and mixtures thereof.

72. Foam formulation according to any one of the preceding embodiments, wherein the emulsion contains at least one active agent.

73. Foam formulation according to embodiment 72, wherein the active agent is selected from the group consisting of hydroviton, pyrrolidone carboxylic acid and salts thereof, lactic acid and salts thereof, glycerol, sorbitol, propylene glycol, urea, collagen, elastin, silk protein, hyaluronic acid, pentavitin, ceramide, panthenol, niacin, α-tocopherol and esters thereof, vitamin A, vitamin C, galates, polyphenols, panthenol, bisabolol, phytosteroles, glucocorticoids, antibiotics, analgesics, antiphlogistics, antirheumatics, antiallergics, antiparasitics, antipruriginostics, antipsoriatics, retinoids, local anaesthetics, therapeutics for the veins, ceratolytics, hyperaemic compounds, coronary therapeutics (nitrates/nitro-compounds), antiviral drugs, cytostatics, hormones, agents promoting wound healing, growth factors, enzyme preparations, insecticides and plant material such as plant extracts of algae, aloe, arnica, barber's rash, comfrey, birch, nettle, calendula, oak, ivy, witch-hazel, henna, hop, camomile, ruscus, peppermint, marigold, rosemary, sage, green tea, tea tree, horse tail, thyme, and walnut or mixtures thereof.

74. Foam formulation according to any one of the preceding embodiments, wherein the foam formulation is a foam cream.

75. Foam formulation according to any one of the preceding embodiments, wherein the foam formulation contains a propellant, preferably a pressure-liquefied propellant.

76. Foam formulation according to embodiment 75, wherein the propellant is selected from the group consisting of $N_2O$, propane, butane, i-butane and mixtures thereof.

77. Foam formulation according to any one of the preceding embodiments, wherein the foam formulation contains from 1 to 20 weight-%, preferably from 2 to 18 weight-%, more preferably from 5 to 15 weight-% of propellant.

78. Foam formulation according to any one of the preceding embodiments, wherein the foam formulation is present in a pressurized container.

79. Use of a substantially emulsifier-free emulsion of the oil-in-water type, comprising an oil phase and an aqueous phase, the emulsion comprising at least one surface active ionic polymer with a molecular weight of more than 5000 g/mol, wherein the ionic polymer is a copolymer comprising as monomer units
an ionic monomer (M1), and
at least one further monomer, for the manufacture of a foam formulation.

80. Use according to embodiment 79 for the manufacture of a foam formulation according to any one of embodiments 1 to 70.

81. Use according to embodiment 79 or 80, wherein the emulsion comprises at least one solid emulsifier.

82. Use of at least one surface active ionic polymer with a molecular weight of more than 5000 g/mol, wherein the ionic polymer is a copolymer comprising as monomer units
an ionic monomer (M1), and
at least one further monomer,
for stabilizing foam formulations comprising a substantially emulsifier-free emulsion of the oil-in-water type.

83. Use according to embodiment 82, wherein the polymer is used in combination with at least one solid emulsifier.

84. Use of a foam formulation according to any one of embodiments 1 to 78 as carrier for an active agent.

85. Use of a foam formulation according to any one of embodiments 1 to 78 as skin care agent.

86. Use of a foam formulation according to any one of embodiments 1 to 78 as skin cleaning agent.

87. Use of a foam formulation according to any one of embodiments 1 to 78 as sunscreen.

88. Use of a foam formulation according to any one of embodiments 1 to 78 for the manufacture of a cosmetic, a medical product or a pharmaceutical composition.

89. Method for manufacturing a foam formulation according to any one of embodiments 1 to 78, comprising the steps of:
a) preparing an emulsion of the oil-in-water type,
b) filling the emulsion with propellant into a pressurized container, or
c) filling the emulsion into a container other than a pressurized container that upon dispensing of the emulsion generates a foam.

90. Method according to embodiment 89, wherein the manufacture of the emulsion comprises the following steps:
(1) providing a liquid oil phase,
(2) providing an aqueous phase comprising at least one surface active, ionic polymer with a molecular weight of more than 5000 g/mol, wherein the ionic polymer is a copolymer comprising as monomer units
an ionic monomer (M1), and
at least one further monomer,
(3) mixing and homogenizing the aqueous phase with the oil phase.

91. Method according to embodiment 90, wherein the oil phase provided in step (1) contains at least one thickener, and/or the aqueous phase provided in step (2) contains at least one thickener and/or the method comprises preferably the following further steps:
(4) providing an aqueous thickener solution,
(5) mixing the thickener solution with the emulsion obtained in step (3).

92. Method according to embodiment 89, wherein the manufacture of the emulsion comprises the following steps:
(1) providing a liquid oil phase,
(2) providing an aqueous phase, (3) mixing and homogenizing the aqueous phase with the oil phase to obtain an emulsion,
(4) providing a further aqueous phase containing at least one surface active, ionic polymer with a molecular weight of more than 5000 g/mol, wherein the ionic polymer is a copolymer comprising as monomer units
an ionic monomer (M1), and
at least one further monomer, ably 5 to 15 weight-% and particularly preferred 10 weight-% of propellant, based on the weight of the foam formulation.

99. Method according to any one of embodiments 89 to 98, wherein the propellant is a pressure-liquefied propellant.

6. Examples

6.1. Examples A

|  | | Example A1 | Example A2 | Example A3 | Example A4 | Example A5 | Example A6 |
|---|---|---|---|---|---|---|---|
| Phase 1: | Miglyol 812 | 5 | 5 | 5 | 5 | 5 | 5 |
| | Cetiol V | 5 | 4 | 4 | 4 | 5 | 5 |
| | Cetiol SN | 5 | 4 | 4 | 4 | 5 | 5 |
| | Eutanol G | 5 | 4 | 4 | 4 | 4 | 4 |
| | Stearic acid | 0 | 1 | 1 | 1 | 1 | 0 |
| | Cutina CP | 0 | 2 | 2 | 2 | 0 | 0 |
| | Cetearyl alcohol | 0 | 0 | 0 | 0 | 0 | 1 |
| Phase 2: | Metholose SH 100 | 0.4 | 0.4 | 0.4 | 0.4 | 0.4 | 0.4 |
| | Urea | 0 | 0 | 0 | 0 | 0 | 0 |
| | Water | 39.6 | 39.6 | 39.6 | 39.6 | 39.6 | 39.6 |
| Phase 3: | Aristoflex HMB | 0 | 0 | 0.4 | 0 | 0 | 0 |
| | Sepinov EMT 10 | 0 | 0 | 0 | 0.4 | 0 | 0 |
| | Aristoflex AVC | 0.4 | 0.4 | 0 | 0 | 0.4 | 0.4 |
| | Water | 39.6 | 39.6 | 39.6 | 39.6 | 39.6 | 39.6 |
| | Total | 100 | 100 | 100 | 100 | 100 | 100 |

The values indicated in the table refer to the weight in grams (g).

(5) mixing the further aqueous phase with the emulsion obtained in step (3).

93. Method according to embodiment 92, wherein the oil phase provided in step (1) contains at least one thickener, and/or the aqueous phase provided in step (2) contains at least one thickener and/or the further aqueous phase provided in step (4) contains at least one thickener, and/or the method comprises preferably the following further steps:
(6) providing an aqueous thickener solution,
(7) mixing the thickener solution with the emulsion obtained in step (5).

94. Method according to embodiment 92 or 93, wherein the mixing of the further aqueous phase with the emulsion in step (5) is performed at a temperature of from 10 to 30° C., preferably of from 15 to 25° C. and particularly preferred at room temperature.

95. Method according to any one of embodiments 90 to 94, wherein the liquid oil phase is provided in step (1) in the form of a clear melt, preferably by heating to a temperature of from 60 to 90° C.

96. Method according to any one of embodiments 90 to 95, wherein the mixing and homogenizing of the aqueous phase with the oil phase in step (3) is performed at a temperature of from 25 to 60° C., preferably of from 30 to 50° C.

97. Method according to any one of embodiments 90 to 96, wherein the liquid oil phase provided in step (1) contains at least one solid emulsifier.

98. Method according to any one of embodiments 89 to 97, wherein the emulsion is charged with 1 to 20 weight-%, preferably 2 to 18 weight-%, more prefer- Manufacture of the O/W-Emulsion/Gel Cream:

The ingredients of phase 1 are heated to 70° C. to obtain a clear melt. After cooling to 40° C., phase 1 is emulsified into phase 2, the latter being heated to 40° C. The mixture is homogenized at 3000 rpm for 5 minutes. After cooling to room temperature, phase 3 is mixed to the obtained emulsion at 1000 rpm.

Manufacture of the Foam Formulation:

90 g of the emulsion are filled into aluminium monoblock cans and are charged with 10.00 g propellant (propane-butane-mixture).

Foam Formation:

A cream foam is formed upon dispensing the foam formulation from the pressurized container by means of a suitable valve having a foam applicator attached.

The following foam qualities are achieved with the formulations of examples A1 to A6:

| | Example A1 | Example A2 | Example A3 | Example A4 | Example A5 | Example A6 |
|---|---|---|---|---|---|---|
| Foam quality | −−[1] | +/−[3] | −[2] | +/−[3] | +/−[3] | +/−[3] |

[1] "−−" means: very coarse-pored foam, collapsing within <1 min;
[2] "−" means: coarse-pored foam collapsing within <1 min;
[3] "+/−" means: coarse- to fine-pored foam collapsing within 1-2 min.

In the case of formulations the foam stability of which is indicated as "+/−", the foam quality may be converted into a "+" by a higher content of emulsifier-copolymer (in the simultaneous presence of a solid substance in the oil phase).

6.2. Examples B

|  |  | Example B1 | Example B2 | Example B3 | Example B4 | Example B5 | Example B6 | Example B7 |
|---|---|---|---|---|---|---|---|---|
| Phase 1: | Cetiol V | 7.5 | 0.0 | 7.5 | 5.0 | 5.0 | 5.0 | 5.0 |
|  | Eutanol G | 7.5 | 0.0 | 0.0 | 0 | 0 | 0 | 0 |
|  | Stearic acid | 3.0 | 3.0 | 3.0 | 3.0 | 3.0 | 3.0 | 3.0 |
|  | Paraffin | 0.0 | 7.5 | 7.5 | 5.0 | 5.0 | 5.0 | 5.0 |
|  | Miglyol 812 | 0.0 | 7.5 | 0.0 | 5.0 | 5.0 | 5.0 | 5.0 |
|  | Xanthan Gum | 0.2 | 0.2 | 0.2 | 0.2 | 0.2 | 0.20 | 0.20 |
|  | Cosmedia SP | 0.1 | 0.1 | 0.1 | 0.2 | 0.2 | 0.20 | 0.20 |
| Phase 2: | Water (ad 100) | 65.3 | 65.3 | 65.3 | 73.7 | 73.7 | 73.7 | 73.7 |
|  | Urea | 11.0 | 11.0 | 11.0 | 5.0 | 5.0 | 5.0 | 5.0 |
|  | Propylene glycol | 2.5 | 2.5 | 2.5 | 0 | 0 | 0 | 0 |
|  | Glycerol 85% | 2.5 | 2.5 | 2.5 | 2.5 | 2.5 | 2.5 | 2.5 |
|  | Aristoflex AVC | 0.4 | 0.4 | 0.4 | 0.4 | 0.0 | 0.0 | 0.0 |
|  | Sepinov EMT 10 | 0.0 | 0.0 | 0.0 | 0.0 | 0.4 | 0.0 | 0.0 |
|  | Seppic 8732 MP | 0.0 | 0.0 | 0.0 | 0.0 | 0.0 | 0.4 | 0.0 |
|  | Seppic 8947 MP | 0.0 | 0.0 | 0.0 | 0.0 | 0.0 | 0.0 | 0.4 |
|  | Total | 100 | 100 | 100 | 100 | 100 | 100 | 100 |

The values indicated in the table refer to the weight in grams (g).

Manufacture of the O/W-Emulsion/Gel Cream:

The lipid components of phase 1 are heated to 70° C. to obtain a clear melt. After cooling to 40° C., the two polymers xanthan gum and Cosmedia SP are dispersed in the oil.

For the manufacture of phase 2, urea, propylene glycol and glycerol are added to the water heated to 40° C. and dissolved therein or blended therewith. The emulsifier-copolymer ("Aristoflex AVC" in examples B1-B4; "Sepinov EMT 10" in example B5; "Seppic 8732 MP" in example B6 or "Seppic 8947 MP" in example B7) is added to the aqueous solution or mixture, and brought into solution with stirring. At 40° C. and 1000 rpm, phase 1 is emulsified into phase 2. Subsequently, the emulsion/gel cream is cooled to room temperature.

Manufacture of the Foam Formulation:

90 g of the emulsion are filled into aluminium monoblock cans and are charged with 10.00 g propellant (propane-butane-mixture).

Foam Formation:

A cream foam is formed upon dispensing the foam formulation from the pressurized container by means of a suitable valve having a foam applicator attached.

The following foam qualities are achieved with the formulations of examples B1 to B7:

| | Example B1 | Example B2 | Example B3 | Example B4 | Example B5 | Example B6 | Example B7 |
|---|---|---|---|---|---|---|---|
| Foam quality | +/−[2] | −[1] | +/−[2] | +[3] | −[1] | +/−[2] | +/−[2] |

[1] "−" means: coarse-pored foam, collapsing within <1 min;
[2] "+/−" means: coarse- to fine-pored foam collapsing within 1-2 min;
[3] "+" means: fine-pored foam collapsing within >2 min.

In the case of formulations the foam stability of which is indicated as "+/−", the foam quality may be converted into a "+" by a higher content of emulsifier-copolymer (in the simultaneous presence of a solid substance in the oil phase).

6.3. Examples C

| | | Example C1 | Example C2 | Example C3 | Example C4 | Example C5 |
|---|---|---|---|---|---|---|
| Phase 1: | Miglyol 812 | 5.0 | 5.0 | 5.0 | 5.0 | 5.0 |
| | Cetiol V | 5.0 | 5.0 | 5.0 | 5.0 | 5.0 |
| | Cetiol SN | 5.0 | 5.0 | 5.0 | 5.0 | 5.0 |
| | Eutanol G | 4.0 | 4.0 | 4.0 | 4.0 | 4.0 |
| | Stearic acid | 1.0 | 1.0 | 1.0 | 1.0 | 1.0 |
| Phase 2: | Metholose SH 100 | 0.4 | 0.4 | 0.4 | 0.4 | 0.4 |
| | Water | 39.6 | 39.6 | 39.6 | 39.6 | 39.6 |
| Phase 3: | Luvimer 100 P | 1.0 | 0 | 0 | 0.5 | 0.5 |
| | Ultrathix p-100 | 0 | 1.0 | 0 | 0 | 0.5 |

-continued

|  | Example C1 | Example C2 | Example C3 | Example C4 | Example C5 |
|---|---|---|---|---|---|
| Aristoflex AVC | 0 | 0 | 1.0 | 0.5 | 0 |
| Trometamol | q.s.[1] | q.s.[1] | q.s.[1] | q.s.[1] | q.s.[1] |
| Water | ad 40.0[2] | ad 40.0[2] | ad 40.0[2] | ad 40.0[2] | ad 40.0[2] |
| Total | 100 | 100 | 100 | 100 | 100 |

[1]q.s. = quantum satis; trometamol is added in an amount to adjust phase 3 to pH 6-7
[2]The amount of water is chosen so that the weight of phase 3 is 40 g.
The values indicated in the table refer to the weight in grams (g).

Manufacture of the O/W-Emulsion/Gel Cream:

The ingredients of phase 1 are heated to 70° C. to obtain a clear melt. After cooling to 40° C., phase 1 is emulsified into phase 2, the latter being heated to 40° C. The mixture is homogenized at 3000 rpm for 5 minutes. After cooling to room temperature, phase 3 (adjusted to pH 6-7) is mixed into the obtained emulsion at 1000 rpm.

Manufacture of the Foam Formulation:

90 g of the emulsion are filled into aluminium monoblock cans and charged with 5.00 g propellant (propane-butane-mixture).

Foam Formation:

A cream foam is formed upon dispensing the foam formulation from the pressurized container by means of a suitable valve having a foam applicator attached.

The following foam qualities are achieved with the formulations of examples C1 to C5:

|  | Example C1 | Example C2 | Example C3 | Example C4 | Example C5 |
|---|---|---|---|---|---|
| Foam quality | +[1] | +[1] | +[1] | ++[2] | +[1] |

[1]"+" means: fine-pored foam collapsing within >2 min;
[2]"++" means: fine-pored foam collapsing within >4 min.

The invention claimed is:

1. A foam comprising an emulsion of the oil-in-water type and a propellant,
   the emulsion comprising an oil phase and an aqueous phase, the emulsion comprising at least one surface active, ionic polymer with a molecular weight of more than 5000 g/mol, wherein the ionic polymer is a copolymer comprising as monomer units
   an ionic monomer (M1), and
   at least one further monomer;
   wherein the emulsion contains less than 0.5 weight-% of conventional emulsifiers, wherein the conventional emulsifiers are amphiphilic substances with a molecular weight of less than 5000 g/mol and which can form a micelle or liquid crystalline aggregate;
   wherein the foam is stable such that it does not collapse for a duration of at least 30 seconds.

2. The foam according to claim 1, wherein the emulsion further comprises at least one solid emulsifier which cannot form a micelle or liquid crystalline aggregate.

3. The foam according to claim 2, wherein the emulsion contains from 0.5 to 7 weight-% of the at least one solid emulsifier, based on the total weight of the emulsion.

4. The foam according to claim 2, wherein the at least one solid emulsifier is a particulate solid emulsifier selected from the group consisting of titanium dioxide, silicon dioxide, $Fe_2O_3$, zinc oxide, veegum, bentonite and ethyl cellulose, aluminum oxide, calcium carbonate, coal, magnesium oxide, magnesium trisilicate, crystalline fatty acids, crystalline fatty acid esters, crystalline fatty alcohols, polymer lattices, and polymer-pseudolattices and mixtures thereof.

5. The foam according to claim 1, wherein the at least one further monomer has a different polarity than the ionic monomer (M1).

6. The foam according to claim 1, wherein the at least one further monomer is selected from the group consisting of ionic monomers, non-ionic monomers, and mixtures thereof.

7. The foam according to claim 1, wherein the ionic monomer (M1) contains free, partially neutralized or completely neutralized acid functional groups.

8. The foam according to claim 1,
   wherein the ionic monomer (M1) is selected from the group consisting of acrylic acids, methacrylic acids, crotonic acids, maleic acids, fumaric acids, styrene sulfonic acids, vinyl sulfonic acids, vinyl phosphonic acids, allyl sulfonic acids, methallyl sulfonic acids, acrylamido alkylsulfonic acids, each of which is present as free acid, as partially or completely neutralized in the form of its salt, or as anhydride, or a mixture thereof.

9. The foam according to claim 1, wherein the ionic monomer (M1) is selected from the group consisting of acrylic acids, methacrylic acids, and acrylamido alkylsulfonic acids.

10. The foam according to claim 1,
    wherein the ionic monomer (M1) is an acrylamido alkylsulfonic acid having the general formula (1),

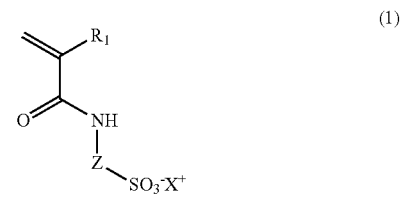

(1)

wherein $R_1$ is selected from the group consisting of hydrogen, methyl, or ethyl, Z is a $(C_1-C_8)$-alkylene, which may be unsubstituted or substituted with one or more $(C_1-C_4)$-alkyl groups, and $X^+$ is selected from the group consisting of $H^+$, an alkali metal ion, an alkaline-earth metal ion, an ammonium ion, an alkanol ammonium ion, and mixtures thereof.

11. The foam according to claim 1, wherein the ionic monomer (M1) is 2-acrylamido-2-methylpropane sulfonic acid having the general formula (2)

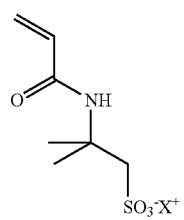

(2)

wherein $R_1$ is selected from the group consisting of hydrogen, methyl, or ethyl, Z is a $(C_1$-$C_8)$-alkylene, which may be unsubstituted or substituted with one or more $(C_1$-$C_4)$-alkyl groups, and $X^+$ is selected from the group consisting of $H^+$, an alkali metal ion, an alkaline-earth metal ion, an ammonium ion, an alkanol ammonium ion, and mixtures thereof.

12. The foam according to claim 1, wherein the at least one further monomer comprises at least one non-ionic monomer selected from the group consisting of styrenes, chlorostyrenes, di-$(C_1$-$C_{30})$-alkylamino styrenes, vinyl chlorides, isoprenes, vinyl alcohols, vinyl methyl ethers, $(C_1$-$C_{30})$-carboxylic acid vinyl esters, acrylic acid esters, methacrylic acid esters, maleic acid esters, fumaric acid esters, crotonic acid esters, linear and branched $(C_1$-$C_{30})$-hydroxyalkyl esters of acrylic acid, methacrylic acid, maleic acid, fumaric acid and crotonic acid, ethoxylated $(C_1$-$C_{30})$-alkyl esters of acrylic acid, methacrylic acid, maleic acid, fumaric acid and crotonic acid with from 1 to 40 ethylene oxide units, acrylamides, and mixtures thereof.

13. The foam according to claim 1, wherein the at least one further monomer comprises at least one ionic monomer selected from the group consisting of acrylic acids, methacrylic acids, crotonic acids, maleic acids, fumaric acids, styrene sulfonic acids, vinyl sulfonic acids, vinyl phosphonic acids, allyl sulfonic acids, methallyl sulfonic acids, acrylamido alkylsulfonic acids, which may each be present as free acid, partially or completely neutralized in the form of their salts, or as an anhydride, and mixtures thereof.

14. The foam according to claim 1, wherein the at least one surface active, ionic polymer is selected from the group consisting of acryloyldimethyltaurate/vinylpyrrolidone copolymer, sodium acrylate/acryloyldimethyltaurate/dimethylacrylamide crosslinked polymer, hydroxyethyl acrylate/sodium acryloyldimethyltaurate copolymer, sodium acrylate/sodium acryloyldimethyltaurate copolymer, and mixtures thereof.

15. The foam according to claim 1, wherein
the ionic monomer (M1) is an acrylic acid and/or methacrylic acid and
the at least one further monomer is selected from the group consisting of cyclic and linear N-vinyl carboxylic acid amides having a carbon chain of 2 to 9 carbon atoms, linear and branched $(C_1$-$C_{30})$-alkyl esters of acrylic acid, linear and branched $(C_1$-$C_{30})$-alkyl esters of methacrylic acid, linear and branched $(C_1$-$C_{30})$-hydroxylalkyl esters of acrylic acid, linear and branched $(C_1$-$C_{30})$-hydroxyalkyl esters of methacrylic acid, and mixtures thereof.

16. The foam according to claim 1, wherein the at least one surface active, ionic polymer comprises a combination of
a) a copolymer of acrylic acid and a cyclic or linear N-vinyl carboxylic acid amide having a carbon chain of 2 to 9 carbon atoms and
b) a copolymer of methacrylic acid and one or more linear or branched $(C_1$-$C_6)$-alkyl esters of acrylic acid.

17. The foam according to claim 1, wherein the at least one surface active ionic polymer comprises acrylic acid/N-vinyl pyrrolidone copolymer and/or tert-butyl acrylate/ethyl acrylate/methacrylic acid terpolymer.

18. A method for manufacturing of a foam according to claim 1, comprising the steps of:
a) preparing an emulsion of the oil-in-water type,
b) filling the emulsion with propellant into a pressurized container, or
c) filling the emulsion into a container other than a pressurized container that upon dispensing of the emulsion generates a foam; and
d) releasing the emulsion and the propellant from the container.

19. The foam according to claim 2, wherein the emulsion contains from 0.5 to 5 weight-% of the at least one solid emulsifier based on the total weight of the emulsion without propellant.

20. The foam according to claim 2, wherein the emulsion contains from 0.5 to 3 weight-% of the at least one solid emulsifier based on the total weight of the emulsion without propellant.

21. The foam according to claim 7, wherein the acid functional groups are selected from the group consisting of sulfonic acid groups, carboxylic acid groups, phosphoric acid groups, phosphonic acid groups, and mixtures thereof.

22. The foam according to claim 8, wherein the ionic monomer is present, partially or completely neutralized, in the form of its alkali metal salt, alkaline-earth metal salt, ammonium salts, or alkanol ammonium salt.

23. The foam according to claim 12, wherein the at least one further monomer comprises at least one non-ionic monomer selected from the group consisting of vinyl acetates and vinyl propionates.

24. The foam according to claim 12, wherein the at least one further monomer comprises at least one non-ionic monomer selected from the group consisting of linear and branched $(C_1$-$C_{30})$-alkyl esters of acrylic acid, methacrylic acid, maleic acid, fumaric acid and crotonic acid, N,N-di-$(C_1$-$C_{30})$-alkyl acrylamides, methacrylamides, N,N-di-$(C_1$-$C_{30})$-alkyl methacrylamides, cyclic and linear N-vinyl carboxylic acid amides with a carbon chain having from 2 to 9 carbon atoms, N-vinylpyrrolidone, and mixtures thereof.

25. The foam according to claim 13, wherein the at least one further monomer is present, partially or completely neutralized, in the form of its alkali metal salt, alkaline-earth metal salt, or ammonium salt.

* * * * *